US008651858B2

(12) United States Patent
Berckmans, III et al.

(10) Patent No.: US 8,651,858 B2
(45) Date of Patent: Feb. 18, 2014

(54) METHOD OF CREATING AN ACCURATE BONE AND SOFT-TISSUE DIGITAL DENTAL MODEL

(75) Inventors: Bruce Berckmans, III, Palm Beach Gardens, FL (US); Zachary B. Suttin, West Palm Beach, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 328 days.

(21) Appl. No.: 12/937,942

(22) PCT Filed: Apr. 13, 2009

(86) PCT No.: PCT/US2009/040375
§ 371 (c)(1),
(2), (4) Date: Feb. 10, 2011

(87) PCT Pub. No.: WO2009/146164
PCT Pub. Date: Dec. 3, 2009

(65) Prior Publication Data
US 2011/0129792 A1 Jun. 2, 2011

Related U.S. Application Data

(60) Provisional application No. 61/124,195, filed on Apr. 15, 2008.

(51) Int. Cl.
*A61C 3/00* (2006.01)
(52) U.S. Cl.
USPC .......................................................... 433/24
(58) Field of Classification Search
USPC .............. 433/24, 215, 72, 75; 705/2, 26
See application file for complete search history.

(56) References Cited

U.S. PATENT DOCUMENTS

| 3,906,634 | A | 9/1975 | Aspel |
| 3,919,772 | A | 11/1975 | Lenczycki ................... 433/173 |
| 3,958,471 | A | 5/1976 | Muller ............................ 82/1.11 |
| 4,011,602 | A | 3/1977 | Rybicki et al. ............. 623/23.76 |
| 4,056,585 | A | 11/1977 | Waltke ............................. 433/74 |
| 4,086,701 | A | 5/1978 | Kawahara et al. ............ 433/174 |
| 4,177,562 | A | 12/1979 | Miller et al. .................. 433/174 |

(Continued)

FOREIGN PATENT DOCUMENTS

| DE | 10029256 | 11/2000 | .............. A61C 1/08 |
| JP | 2003088537 | 3/2003 | |

(Continued)

OTHER PUBLICATIONS

BIOMET3i Navigator™; "Navigator™ System for CT Guided Surgery Manual", pp. 1-26, Oct. 2007.

(Continued)

*Primary Examiner* — Sunil K Singh
(74) *Attorney, Agent, or Firm* — Nixon Peabody LLP

(57) ABSTRACT

A method of creating a 3-D anatomic digital model for determining a desired location for placing at least one dental implant in a patient's mouth. The method comprises the act of obtaining a first dataset associated with hard tissue of the patient's mouth. The method further comprises the act of obtaining a second dataset associated with soft tissue of the patient's mouth. The method further comprises the act of combining the first dataset and the second dataset to create a detailed structure of hard tissue and soft tissue having variable dimensions over the hard tissue.

20 Claims, 15 Drawing Sheets

(56) References Cited

U.S. PATENT DOCUMENTS

| | | | |
|---|---|---|---|
| 4,294,544 A | 10/1981 | Altschuler et al. | 356/610 |
| 4,306,862 A | 12/1981 | Knox | 433/77 |
| 4,325,373 A | 4/1982 | Slivenko et al. | |
| 4,341,312 A | 7/1982 | Scholer | 211/70.6 |
| 4,364,381 A | 12/1982 | Sher et al. | |
| 4,439,152 A | 3/1984 | Small | |
| 4,543,953 A | 10/1985 | Slocum et al. | |
| 4,547,157 A | 10/1985 | Driskell | 433/173 |
| 4,571,180 A | 2/1986 | Kulick | |
| 4,611,288 A | 9/1986 | Duret | 700/163 |
| 4,624,673 A | 11/1986 | Meyer | 433/173 |
| 4,663,720 A | 5/1987 | Duret | 700/163 |
| 4,713,004 A | 12/1987 | Linkow et al. | 433/174 |
| 4,756,689 A | 7/1988 | Lundgren et al. | |
| 4,758,161 A | 7/1988 | Niznick | 433/173 |
| 4,767,331 A | 8/1988 | Hoe | 433/213 |
| 4,772,204 A | 9/1988 | Soderberg | 433/174 |
| 4,821,200 A | 4/1989 | Oberg | 700/182 |
| 4,842,518 A | 6/1989 | Linkow et al. | 433/174 |
| 4,850,870 A | 7/1989 | Lazzara et al. | 433/174 |
| 4,850,873 A | 7/1989 | Lazzara et al. | 433/220 |
| 4,854,872 A | 8/1989 | Detsch | 433/173 |
| 4,856,994 A | 8/1989 | Lazzara et al. | 433/173 |
| 4,872,839 A | 10/1989 | Brajnovic | |
| 4,906,191 A | 3/1990 | Soderberg | 433/213 |
| 4,906,420 A | 3/1990 | Brajnovic et al. | |
| 4,931,016 A | 6/1990 | Sillard | |
| 4,935,635 A | 6/1990 | O'Harra | 250/559.06 |
| 4,961,674 A | 10/1990 | Wang et al. | |
| 4,964,770 A | 10/1990 | Steinbichler | 433/223 |
| 4,986,753 A | 1/1991 | Sellers | |
| 4,988,297 A | 1/1991 | Lazzara et al. | |
| 4,998,881 A | 3/1991 | Lauks | |
| 5,000,685 A | 3/1991 | Brajnovic | |
| 5,006,069 A | 4/1991 | Lazzara et al. | 433/173 |
| 5,015,183 A | 5/1991 | Fenick | |
| 5,015,186 A | 5/1991 | Detsch | |
| 5,030,096 A | 7/1991 | Hurson et al. | 433/173 |
| 5,035,619 A | 7/1991 | Daftary | 433/173 |
| 5,040,982 A | 8/1991 | Stefan-Dogar | |
| 5,040,983 A | 8/1991 | Binon | 433/173 |
| 5,064,375 A | 11/1991 | Jorneus | 433/229 |
| 5,071,351 A | 12/1991 | Green, Jr. et al. | 433/173 |
| 5,073,111 A | 12/1991 | Daftary | 433/173 |
| 5,087,200 A | 2/1992 | Brajnovic et al. | |
| 5,100,323 A | 3/1992 | Friedman et al. | 433/173 |
| 5,104,318 A | 4/1992 | Piche et al. | 433/174 |
| 5,106,300 A | 4/1992 | Voitik | 433/173 |
| 5,122,059 A | 6/1992 | Durr et al. | 433/173 |
| 5,125,839 A | 6/1992 | Ingber et al. | 433/169 |
| 5,125,841 A | 6/1992 | Carlsson et al. | 433/213 |
| 5,133,660 A | 7/1992 | Fenick | |
| 5,135,395 A | 8/1992 | Marlin | 433/174 |
| 5,145,371 A | 9/1992 | Jorneus | 433/173 |
| 5,145,372 A | 9/1992 | Daftary | 433/173 |
| 5,176,516 A | 1/1993 | Koizumi | |
| 5,188,800 A | 2/1993 | Green, Jr. et al. | 134/1 |
| 5,195,892 A | 3/1993 | Gersberg | 433/174 |
| 5,205,745 A | 4/1993 | Kamiya et al. | 433/173 |
| 5,209,659 A | 5/1993 | Friedman et al. | 433/173 |
| 5,209,666 A | 5/1993 | Balfour et al. | 433/173 |
| 5,213,502 A | 5/1993 | Daftary | 433/172 |
| 5,221,204 A | 6/1993 | Kruger et al. | 433/173 |
| 5,237,998 A | 8/1993 | Duret et al. | 600/476 |
| 5,246,370 A | 9/1993 | Coatoam | |
| 5,257,184 A | 10/1993 | Mushabac | 433/75 |
| 5,281,140 A | 1/1994 | Niznick | 433/172 |
| 5,286,195 A | 2/1994 | Clostermann | 433/172 |
| 5,286,196 A | 2/1994 | Brajnovic et al. | |
| 5,292,252 A | 3/1994 | Nickerson et al. | 433/173 |
| 5,297,963 A | 3/1994 | Dafatry | 433/172 |
| 5,302,125 A | 4/1994 | Kownacki et al. | |
| 5,312,254 A | 5/1994 | Rosenlicht | 433/173 |
| 5,312,409 A | 5/1994 | McLaughlin et al. | |
| 5,316,476 A | 5/1994 | Krauser | 433/173 |
| 5,320,529 A | 6/1994 | Pompa | |
| 5,328,371 A | 7/1994 | Hund et al. | |
| 5,334,024 A | 8/1994 | Niznick | 433/173 |
| 5,336,090 A | 8/1994 | Wilson, Jr. et al. | 433/172 |
| 5,338,196 A | 8/1994 | Beaty et al. | 433/172 |
| 5,338,198 A | 8/1994 | Wu et al. | 433/213 |
| 5,343,391 A | 8/1994 | Mushabac | 433/76 |
| 5,344,457 A | 9/1994 | Pilliar et al. | 606/60 |
| 5,350,297 A | 9/1994 | Cohen | |
| 5,359,511 A | 10/1994 | Schroeder et al. | 433/75 |
| 5,362,234 A | 11/1994 | Salazar et al. | 433/169 |
| 5,362,235 A | 11/1994 | Daftary | 433/172 |
| 5,368,483 A | 11/1994 | Sutter et al. | 433/173 |
| 5,370,692 A | 12/1994 | Fink et al. | 128/898 |
| 5,372,502 A | 12/1994 | Massen et al. | 433/215 |
| 5,386,292 A | 1/1995 | Massen et al. | 356/603 |
| 5,413,481 A | 5/1995 | Goppel et al. | 433/214 |
| 5,417,569 A | 5/1995 | Perisse | |
| 5,417,570 A | 5/1995 | Zuest et al. | 433/177 |
| 5,419,702 A | 5/1995 | Beaty et al. | 433/214 |
| 5,431,567 A | 7/1995 | Daftary | 433/172 |
| 5,437,551 A | 8/1995 | Chalifoux | 433/173 |
| 5,440,393 A | 8/1995 | Wenz | 356/611 |
| 5,452,219 A | 9/1995 | Dehoff et al. | 700/163 |
| 5,458,488 A | 10/1995 | Chalifoux | 433/173 |
| 5,476,382 A | 12/1995 | Daftary | 433/172 |
| 5,476,383 A | 12/1995 | Beaty et al. | 433/214 |
| 5,492,471 A | 2/1996 | Singer | 433/172 |
| 5,516,288 A | 5/1996 | Sichler et al. | |
| 5,527,182 A | 6/1996 | Willoughby | |
| 5,533,898 A | 7/1996 | Mena | 433/173 |
| 5,538,426 A | 7/1996 | Harding et al. | 433/172 |
| 5,547,377 A | 8/1996 | Daftary | 433/172 |
| 5,556,278 A | 9/1996 | Meitner | |
| 5,564,921 A | 10/1996 | Marlin | 433/172 |
| 5,564,924 A | 10/1996 | Kwan | 433/173 |
| 5,569,578 A | 10/1996 | Mushabac | 433/215 |
| 5,575,656 A | 11/1996 | Hajjar | |
| 5,580,244 A | 12/1996 | White | 433/37 |
| 5,580,246 A | 12/1996 | Fried et al. | |
| 5,595,703 A | 1/1997 | Swaelens | 264/401 |
| 5,613,832 A | 3/1997 | Su | |
| 5,613,852 A | 3/1997 | Bravitz | |
| 5,630,717 A | 5/1997 | Zuest et al. | |
| 5,636,986 A | 6/1997 | Pezeshkian | |
| 5,651,675 A | 7/1997 | Singer | 433/172 |
| 5,652,709 A | 7/1997 | Andersson | 700/161 |
| 5,658,147 A | 8/1997 | Phimmasone | 433/213 |
| 5,662,476 A | 9/1997 | Ingber et al. | |
| 5,674,069 A | 10/1997 | Osorio | 433/172 |
| 5,674,071 A | 10/1997 | Beaty et al. | 433/172 |
| 5,674,073 A | 10/1997 | Ingber et al. | 433/213 |
| 5,681,167 A | 10/1997 | Lazarof | 433/174 |
| 5,685,715 A | 11/1997 | Beaty et al. | 433/173 |
| 5,688,283 A | 11/1997 | Knapp | |
| 5,704,936 A | 1/1998 | Mazel | |
| 5,718,579 A | 2/1998 | Kennedy | |
| 5,725,376 A | 3/1998 | Poirier | |
| 5,733,124 A | 3/1998 | Kwan | |
| 5,741,215 A | 4/1998 | D'Urso | 600/407 |
| 5,743,916 A | 4/1998 | Greenberg et al. | |
| 5,759,036 A | 6/1998 | Hinds | 433/214 |
| 5,762,125 A | 6/1998 | Mastrorio | 164/4.1 |
| 5,762,500 A | 6/1998 | Lazarof | |
| 5,768,134 A | 6/1998 | Swaelens et al. | |
| 5,769,636 A | 6/1998 | Di Sario | |
| 5,791,902 A | 8/1998 | Lauks | |
| 5,800,168 A | 9/1998 | Cascione et al. | |
| 5,813,858 A | 9/1998 | Singer | 433/173 |
| 5,823,778 A | 10/1998 | Schmitt | 433/214 |
| 5,842,859 A | 12/1998 | Palacci | |
| 5,846,079 A | 12/1998 | Knode | |
| 5,851,115 A | 12/1998 | Carlsson et al. | 433/215 |
| 5,857,853 A | 1/1999 | van Nifterick et al. | 433/213 |
| 5,871,358 A | 2/1999 | Ingber et al. | |
| 5,873,722 A | 2/1999 | Lazzara et al. | 433/173 |
| 5,876,204 A | 3/1999 | Day et al. | |
| 5,885,078 A | 3/1999 | Cagna et al. | |
| 5,888,034 A | 3/1999 | Greenberg | |

(56) References Cited

U.S. PATENT DOCUMENTS

| | | | |
|---|---|---|---|
| 5,904,483 A | 5/1999 | Wade | |
| 5,915,962 A | 6/1999 | Rosenlicht | |
| 5,927,982 A | 7/1999 | Kruger | |
| 5,938,443 A | 8/1999 | Lazzara et al. | 433/173 |
| 5,954,769 A | 9/1999 | Rosenlicht | |
| 5,964,591 A | 10/1999 | Beaty et al. | |
| 5,967,777 A | 10/1999 | Klein et al. | |
| 5,984,681 A | 11/1999 | Huang | |
| 5,989,025 A | 11/1999 | Conley | |
| 5,989,029 A | 11/1999 | Osorio et al. | 433/173 |
| 5,989,258 A | 11/1999 | Hattori | |
| 5,997,681 A | 12/1999 | Kinzie | 156/263 |
| 6,000,939 A | 12/1999 | Ray et al. | |
| 6,008,905 A | 12/1999 | Breton et al. | 356/402 |
| 6,068,479 A | 5/2000 | Kwan | |
| 6,099,311 A | 8/2000 | Wagner et al. | |
| 6,099,313 A | 8/2000 | Dorken et al. | |
| 6,099,314 A | 8/2000 | Kopelman et al. | 433/213 |
| 6,120,293 A | 9/2000 | Lazzara et al. | 433/173 |
| 6,129,548 A | 10/2000 | Lazzara et al. | 433/172 |
| 6,135,773 A | 10/2000 | Lazzara | |
| 6,142,782 A | 11/2000 | Lazarof | |
| 6,174,168 B1 | 1/2001 | Dehoff et al. | 433/202.1 |
| 6,175,413 B1 | 1/2001 | Lucas | 356/614 |
| 6,190,169 B1 | 2/2001 | Bluemli et al. | |
| 6,197,410 B1 | 3/2001 | Vallittu et al. | |
| 6,200,125 B1 | 3/2001 | Akutagawa | 425/462 |
| 6,206,693 B1 | 3/2001 | Hultgren | 433/38 |
| 6,210,162 B1 | 4/2001 | Chishti et al. | 433/213 |
| 6,217,334 B1 | 4/2001 | Hultgren | 433/215 |
| 6,227,859 B1 | 5/2001 | Sutter | |
| 6,283,753 B1 | 9/2001 | Willoughby | 433/172 |
| 6,287,119 B1 | 9/2001 | van Nifterick et al. | |
| 6,296,483 B1 | 10/2001 | Champleboux | |
| 6,319,000 B1 | 11/2001 | Branemark | |
| 6,322,728 B1 | 11/2001 | Brodkin et al. | 264/19 |
| 6,382,975 B1 | 5/2002 | Poirier | |
| 6,402,707 B1 | 6/2002 | Ernst | 600/590 |
| 6,488,503 B1 | 12/2002 | Lichkus et al. | 433/202 |
| 6,497,574 B1 | 12/2002 | Miller | 433/213 |
| 6,540,784 B2 | 4/2003 | Barlow et al. | 623/16.11 |
| 6,568,936 B2 | 5/2003 | MacDougald et al. | |
| 6,575,751 B1 | 6/2003 | Lehmann et al. | 433/223 |
| 6,594,539 B1 | 7/2003 | Geng | 700/117 |
| 6,610,079 B1 | 8/2003 | Li et al. | |
| 6,619,958 B2 | 9/2003 | Beaty et al. | 433/173 |
| 6,629,840 B2 | 10/2003 | Chishti et al. | 433/24 |
| 6,634,883 B2 | 10/2003 | Ranalli | |
| 6,648,640 B2 | 11/2003 | Rubbert et al. | 433/24 |
| 6,671,539 B2 | 12/2003 | Gateno et al. | 600/426 |
| 6,672,870 B2 | 1/2004 | Knapp | |
| 6,688,887 B2 | 2/2004 | Morgan | |
| 6,691,764 B2 | 2/2004 | Embert et al. | 164/4.1 |
| 6,743,491 B2 | 6/2004 | Cirincione et al. | |
| 6,755,652 B2 | 6/2004 | Nanni | |
| 6,772,026 B2 | 8/2004 | Bradbury et al. | 700/98 |
| 6,776,614 B2 | 8/2004 | Wiechmann et al. | 433/24 |
| 6,783,359 B2 | 8/2004 | Kapit | |
| 6,790,040 B2 | 9/2004 | Amber et al. | 433/173 |
| 6,793,491 B2 | 9/2004 | Klein et al. | |
| 6,808,659 B2 | 10/2004 | Schulman et al. | 264/16 |
| 6,814,575 B2 | 11/2004 | Poirier | 433/75 |
| 6,821,462 B2 | 11/2004 | Schulman et al. | 264/16 |
| 6,829,498 B2 | 12/2004 | Kipke et al. | 600/378 |
| D503,804 S | 4/2005 | Phleps et al. | |
| 6,882,894 B2 | 4/2005 | Durbin et al. | 700/118 |
| 6,885,464 B1 | 4/2005 | Pfeiffer et al. | |
| 6,902,401 B2 | 6/2005 | Jorneus | |
| 6,913,463 B2 | 7/2005 | Blacklock | |
| 6,926,442 B2 | 8/2005 | Stöckl | |
| 6,926,525 B1 | 8/2005 | Ronrig et al. | |
| 6,939,489 B2 | 9/2005 | Moszner et al. | 264/16 |
| 6,942,699 B2 | 9/2005 | Stone et al. | |
| 6,953,383 B2 | 10/2005 | Rothenberger | |
| 6,957,118 B2 | 10/2005 | Kopelman et al. | 700/118 |
| 6,966,772 B2 | 11/2005 | Malin et al. | |
| 6,970,760 B2 | 11/2005 | Wolf et al. | 700/163 |
| 6,971,877 B2 | 12/2005 | Harter | |
| 6,994,549 B2 | 2/2006 | Brodkin et al. | 433/202.1 |
| 7,010,150 B1 | 3/2006 | Pfeiffer et al. | |
| 7,010,153 B2 | 3/2006 | Zimmermann | |
| 7,012,988 B2 | 3/2006 | Adler et al. | |
| 7,018,207 B2 | 3/2006 | Prestipino | |
| 7,021,934 B2 | 4/2006 | Aravena | |
| 7,029,275 B2 | 4/2006 | Rubbert et al. | 433/24 |
| 7,044,735 B2 | 5/2006 | Malin | |
| 7,056,115 B2 | 6/2006 | Phan et al. | 433/24 |
| 7,056,472 B1 | 6/2006 | Behringer | |
| 7,059,856 B2 | 6/2006 | Marotta | |
| 7,066,736 B2 | 6/2006 | Kumar et al. | |
| 7,084,868 B2 | 8/2006 | Farag et al. | |
| 7,086,860 B2 | 8/2006 | Schuman et al. | |
| 7,097,451 B2 | 8/2006 | Tang | |
| 7,104,795 B2 | 9/2006 | Dadi | |
| 7,110,844 B2 | 9/2006 | Kopelman et al. | 700/118 |
| 7,112,065 B2 | 9/2006 | Kopelman et al. | 433/213 |
| 7,118,375 B2 | 10/2006 | Durbin et al. | 433/68 |
| D532,991 S | 12/2006 | Gozzi | |
| 7,153,132 B2 | 12/2006 | Tedesco | |
| 7,153,135 B1 | 12/2006 | Thomas | 433/213 |
| 7,163,443 B2 | 1/2007 | Basler et al. | |
| 7,175,434 B2 | 2/2007 | Brajnovic | |
| 7,175,435 B2 | 2/2007 | Andersson et al. | |
| 7,178,731 B2 | 2/2007 | Basler | |
| 7,214,062 B2 | 5/2007 | Morgan | |
| 7,220,124 B2 | 5/2007 | Taub et al. | 433/213 |
| 7,228,191 B2 | 6/2007 | Hofmeister et al. | 700/98 |
| 7,236,842 B2 | 6/2007 | Kopelman et al. | 700/98 |
| 7,281,927 B2 | 10/2007 | Marotta | |
| 7,286,954 B2 | 10/2007 | Kopelman et al. | 702/152 |
| 7,303,420 B2 | 12/2007 | Huch et al. | |
| 7,319,529 B2 | 1/2008 | Babayoff | 356/601 |
| 7,322,746 B2 | 1/2008 | Beckhaus et al. | |
| 7,322,824 B2 | 1/2008 | Schmitt | 433/215 |
| 7,324,680 B2 | 1/2008 | Zimmermann | |
| 7,329,122 B1 | 2/2008 | Scott | |
| 7,333,874 B2 | 2/2008 | Taub et al. | 700/117 |
| 7,335,876 B2 | 2/2008 | Eiff et al. | |
| D565,184 S | 3/2008 | Royzen | |
| 7,367,801 B2 | 5/2008 | Saliger | |
| 7,379,584 B2 | 5/2008 | Rubbert et al. | 382/154 |
| D571,471 S | 6/2008 | Stöckl | |
| 7,381,191 B2 | 6/2008 | Fallah | |
| 7,383,094 B2 | 6/2008 | Kopelman et al. | 700/118 |
| D575,747 S | 8/2008 | Abramovich et al. | |
| 7,421,608 B2 | 9/2008 | Schron | |
| 7,429,175 B2 | 9/2008 | Gittelson | |
| 7,435,088 B2 | 10/2008 | Brajnovic | |
| 7,476,100 B2 | 1/2009 | Kuo | 433/6 |
| 7,481,647 B2 | 1/2009 | Sambu et al. | 425/436 |
| 7,488,174 B2 | 2/2009 | Kopelman et al. | 433/213 |
| 7,497,619 B2 | 3/2009 | Stoeckl | |
| 7,497,983 B2 | 3/2009 | Khan et al. | 264/673 |
| 7,520,747 B2 | 4/2009 | Stonisch | |
| 7,522,764 B2 | 4/2009 | Schwotzer | |
| 7,534,266 B2 | 5/2009 | Kluger | |
| 7,536,234 B2 | 5/2009 | Kopelman et al. | 700/118 |
| 7,545,372 B2 | 6/2009 | Kopelman et al. | 345/419 |
| 7,551,760 B2 | 6/2009 | Scharlack et al. | |
| 7,555,403 B2 | 6/2009 | Kopelman et al. | 702/152 |
| 7,556,496 B2 | 7/2009 | Cinader, Jr. et al. | 433/24 |
| 7,559,692 B2 | 7/2009 | Beckhaus et al. | |
| 7,563,397 B2 | 7/2009 | Schulman et al. | 264/16 |
| D597,769 S | 8/2009 | Richter et al. | |
| 7,572,058 B2 | 8/2009 | Pruss et al. | |
| 7,572,125 B2 | 8/2009 | Brajnovic | |
| 7,574,025 B2 | 8/2009 | Feldman | 382/128 |
| 7,578,673 B2 | 8/2009 | Wen et al. | 433/24 |
| 7,580,502 B2 | 8/2009 | Dalpiaz et al. | |
| 7,581,951 B2 | 9/2009 | Lehmann et al. | |
| 7,582,855 B2 | 9/2009 | Pfeiffer | |
| 7,628,537 B2 | 12/2009 | Schulze-Ganzlin | |
| 7,632,097 B2 | 12/2009 | Clerck | 433/215 |
| 7,653,455 B2 | 1/2010 | Cinader, Jr. | |

(56) References Cited

U.S. PATENT DOCUMENTS

| | | | |
|---|---|---|---|
| 7,654,823 B2 | 2/2010 | Dadi | |
| 7,655,586 B1 | 2/2010 | Brodkin et al. | 501/103 |
| 7,658,610 B2 | 2/2010 | Knopp | 433/24 |
| 7,661,956 B2 | 2/2010 | Powell et al. | 433/172 |
| 7,665,989 B2 | 2/2010 | Brajnovic et al. | |
| 7,679,723 B2 | 3/2010 | Schwotzer | |
| 7,687,754 B2 | 3/2010 | Eiff et al. | |
| 7,689,308 B2 | 3/2010 | Holzner et al. | |
| D614,210 S | 4/2010 | Basler et al. | |
| 7,698,014 B2 | 4/2010 | Dunne et al. | |
| 7,774,084 B2 | 8/2010 | Cinader, Jr. | |
| 7,780,907 B2 | 8/2010 | Schmidt et al. | |
| 7,785,007 B2 | 8/2010 | Stoeckl | |
| 7,787,132 B2 | 8/2010 | Körner et al. | |
| 7,796,811 B2 | 9/2010 | Orth et al. | |
| 7,798,708 B2 | 9/2010 | Erhardt et al. | |
| 7,801,632 B2 | 9/2010 | Orth et al. | |
| 7,815,371 B2 | 10/2010 | Schulze-Ganzlin | |
| 7,824,181 B2 | 11/2010 | Sers | |
| D629,908 S | 12/2010 | Jerger et al. | |
| 7,855,354 B2 | 12/2010 | Eiff | |
| 7,865,261 B2 | 1/2011 | Pfeiffer | |
| 7,876,877 B2 | 1/2011 | Stockl | |
| 7,901,209 B2 | 3/2011 | Saliger et al. | |
| 7,982,731 B2 | 7/2011 | Orth et al. | |
| 7,985,119 B2 | 7/2011 | Basler et al. | |
| 7,986,415 B2 | 7/2011 | Thiel et al. | |
| 8,026,943 B2 | 9/2011 | Weber et al. | |
| 8,038,440 B2 | 10/2011 | Swaelens et al. | 433/76 |
| 8,047,895 B2 | 11/2011 | Basler | |
| 8,057,912 B2 | 11/2011 | Basler et al. | |
| 8,062,034 B2 | 11/2011 | Hanisch et al. | |
| 8,083,522 B2 | 12/2011 | Karkar et al. | |
| 8,105,081 B2 | 1/2012 | Bavar | 433/75 |
| 2001/0008751 A1 | 7/2001 | Chishti et al. | |
| 2001/0034010 A1 | 10/2001 | MacDougald et al. | 433/223 |
| 2002/0010568 A1 | 1/2002 | Rubbert et al. | 703/6 |
| 2002/0028418 A1 | 3/2002 | Farag et al. | 433/29 |
| 2002/0160337 A1 | 10/2002 | Klein et al. | |
| 2002/0167100 A1 | 11/2002 | Moszner et al. | 264/16 |
| 2003/0130605 A1 | 7/2003 | Besek | |
| 2003/0222366 A1 | 12/2003 | Stangel et al. | 264/16 |
| 2004/0029074 A1 | 2/2004 | Brajnovic | |
| 2004/0048227 A1 | 3/2004 | Brajnovic | |
| 2004/0219477 A1 | 11/2004 | Harter | |
| 2004/0219479 A1 | 11/2004 | Malin et al. | |
| 2004/0219490 A1 | 11/2004 | Gartner et al. | 433/218 |
| 2004/0220691 A1 | 11/2004 | Hofmeister et al. | 700/98 |
| 2004/0243481 A1* | 12/2004 | Bradbury et al. | 705/26 |
| 2004/0259051 A1 | 12/2004 | Brajnovic | |
| 2005/0023710 A1 | 2/2005 | Brodkin et al. | 264/16 |
| 2005/0056350 A1 | 3/2005 | Dolabdjian et al. | 148/512 |
| 2005/0070782 A1 | 3/2005 | Brodkin | 600/407 |
| 2005/0084144 A1 | 4/2005 | Feldman | 382/128 |
| 2005/0100861 A1 | 5/2005 | Choi | |
| 2005/0170311 A1 | 8/2005 | Tardieu | |
| 2005/0271996 A1 | 12/2005 | Sporbert et al. | 433/24 |
| 2005/0277089 A1 | 12/2005 | Brajnovic | |
| 2005/0277090 A1 | 12/2005 | Anderson et al. | |
| 2005/0277091 A1 | 12/2005 | Andersson et al. | |
| 2005/0282106 A1 | 12/2005 | Sussman et al. | |
| 2005/0283065 A1* | 12/2005 | Babayoff | 600/407 |
| 2006/0006561 A1 | 1/2006 | Brajnovic | |
| 2006/0008763 A1 | 1/2006 | Brajnovic | |
| 2006/0008770 A1 | 1/2006 | Brajnovic et al. | |
| 2006/0093988 A1 | 5/2006 | Swaelens et al. | |
| 2006/0094951 A1 | 5/2006 | Dean et al. | 600/407 |
| 2006/0127848 A1 | 6/2006 | Sogo et al. | |
| 2006/0210949 A1 | 9/2006 | Stoop | |
| 2006/0263741 A1 | 11/2006 | Imgrund et al. | 433/24 |
| 2006/0281041 A1 | 12/2006 | Rubbert et al. | 433/24 |
| 2007/0015111 A1 | 1/2007 | Kopelman et al. | 433/213 |
| 2007/0031790 A1 | 2/2007 | Raby et al. | 433/213 |
| 2007/0065777 A1 | 3/2007 | Becker | |
| 2007/0077532 A1 | 4/2007 | Harter | |
| 2007/0092854 A1 | 4/2007 | Powell et al. | 433/213 |
| 2007/0141525 A1 | 6/2007 | Cinader, Jr. et al. | 433/23 |
| 2007/0190481 A1* | 8/2007 | Schmitt | 433/68 |
| 2007/0211081 A1 | 9/2007 | Quadling et al. | 345/632 |
| 2007/0218426 A1 | 9/2007 | Quadling et al. | 433/223 |
| 2007/0269769 A1 | 11/2007 | Marchesi | 433/215 |
| 2007/0281277 A1 | 12/2007 | Brajnovic | |
| 2008/0038692 A1 | 2/2008 | Andersson et al. | |
| 2008/0044794 A1 | 2/2008 | Brajnovic | |
| 2008/0057467 A1 | 3/2008 | Gittelson | |
| 2008/0070181 A1 | 3/2008 | Abolfathi et al. | 433/6 |
| 2008/0085489 A1 | 4/2008 | Schmitt | |
| 2008/0090210 A1 | 4/2008 | Brajnovic | |
| 2008/0114371 A1 | 5/2008 | Kluger | |
| 2008/0118895 A1 | 5/2008 | Brajnovic | |
| 2008/0124676 A1 | 5/2008 | Marotta | |
| 2008/0153060 A1 | 6/2008 | De Moyer | 433/173 |
| 2008/0153061 A1 | 6/2008 | Marcello | 433/173 |
| 2008/0153065 A1 | 6/2008 | Brajnovic | |
| 2008/0153069 A1 | 6/2008 | Holzner et al. | 433/223 |
| 2008/0176189 A1 | 7/2008 | Stonisch | |
| 2008/0206714 A1 | 8/2008 | Schmitt | 433/215 |
| 2008/0241798 A1 | 10/2008 | Holzner et al. | 433/223 |
| 2008/0261165 A1 | 10/2008 | Steingart et al. | 433/24 |
| 2008/0300716 A1 | 12/2008 | Kopelman et al. | 700/182 |
| 2009/0017418 A1 | 1/2009 | Gittelson | |
| 2009/0026643 A1 | 1/2009 | Wiest et al. | 264/16 |
| 2009/0042167 A1 | 2/2009 | Van Der Zel | 433/215 |
| 2009/0081616 A1 | 3/2009 | Pfeiffer | 433/215 |
| 2009/0087817 A1 | 4/2009 | Jansen et al. | 433/223 |
| 2009/0092948 A1 | 4/2009 | Gantes | |
| 2009/0098510 A1 | 4/2009 | Zhang | 433/201.1 |
| 2009/0098511 A1 | 4/2009 | Zhang | 433/201.1 |
| 2009/0123045 A1 | 5/2009 | Quadling et al. | 382/128 |
| 2009/0123887 A1 | 5/2009 | Brajnovic | |
| 2009/0187393 A1 | 7/2009 | Van Lierde et al. | |
| 2009/0220134 A1 | 9/2009 | Cahill et al. | |
| 2009/0220916 A1 | 9/2009 | Fisker et al. | 433/201.1 |
| 2009/0220917 A1 | 9/2009 | Jensen | 433/202.1 |
| 2009/0239197 A1 | 9/2009 | Brajnovic | |
| 2009/0239200 A1 | 9/2009 | Brajnovic et al. | |
| 2009/0253097 A1 | 10/2009 | Brajnovic | |
| 2009/0287332 A1 | 11/2009 | Adusumilli et al. | 700/98 |
| 2009/0298009 A1 | 12/2009 | Brajnovic | |
| 2009/0298017 A1 | 12/2009 | Boerjes et al. | 433/214 |
| 2009/0317763 A1 | 12/2009 | Brajnovic | |
| 2009/0325122 A1 | 12/2009 | Brajnovic et al. | |
| 2010/0009314 A1 | 1/2010 | Tardieu et al. | |
| 2010/0028827 A1 | 2/2010 | Andersson et al. | |
| 2010/0038807 A1 | 2/2010 | Brodkin et al. | 264/17 |
| 2010/0075275 A1 | 3/2010 | Brainovic | |
| 2010/0092904 A1 | 4/2010 | Esposti et al. | |
| 2010/0173260 A1 | 7/2010 | Sogo et al. | |
| 2010/0280798 A1 | 11/2010 | Pattijn et al. | |
| 2011/0008751 A1 | 1/2011 | Pettersson | |
| 2011/0060558 A1 | 3/2011 | Pettersson et al. | |
| 2011/0191081 A1 | 8/2011 | Malfliet et al. | |
| 2011/0275032 A1 | 11/2011 | Tardieu et al. | |
| 2012/0010740 A1 | 1/2012 | Swaelens et al. | |
| 2012/0164593 A1 | 6/2012 | Bavar | 433/29 |
| 2012/0164893 A1 | 6/2012 | Mitsuzuka et al. | 439/692 |

FOREIGN PATENT DOCUMENTS

| | | | |
|---|---|---|---|
| JP | 2005532838 | 11/2005 | |
| WO | WO 94/26200 | 11/1994 | A61C 1/08 |
| WO | WO99/32045 | 7/1999 | |
| WO | WO 00/08415 | 2/2000 | A61B 5/107 |
| WO | WO 01/58379 | 8/2001 | |
| WO | WO 02/053055 | 7/2002 | |
| WO | WO 03/024352 | 3/2003 | A61C 8/00 |
| WO | WO 03060825 | 7/2003 | |
| WO | WO 2004/030565 | 4/2004 | A61C 13/00 |
| WO | WO2004/075771 | 10/2004 | |
| WO | WO 2004/087000 | 10/2004 | A61C 13/00 |
| WO | WO2004/098435 | 11/2004 | |
| WO | WO2006/014130 | 2/2006 | |
| WO | WO2006/062459 | 6/2006 | |
| WO | WO2006/082198 | 10/2006 | |

(56) References Cited

FOREIGN PATENT DOCUMENTS

| WO | WO2007/033157 | 3/2007 |
|----|---------------|--------|
| WO | WO2007/104842 | 9/2007 |
| WO | WO2007/129955 | 11/2007 |
| WO | WO 2008/024450 | 2/2008 |
| WO | WO2008/057955 | 5/2008 |
| WO | WO2008/083857 | 7/2008 |

OTHER PUBLICATIONS

Imaterialise Medical; :Surgical Guide Cookbook, Brill Guides for Every Scenario; pp. 1-87, Date unknown.
International Preliminary Report on Patentability corresponding to co-pending International Patent Application Serial No. PCT/US09/40375 Patent Office, Dated Apr. 13, 2009.

* cited by examiner

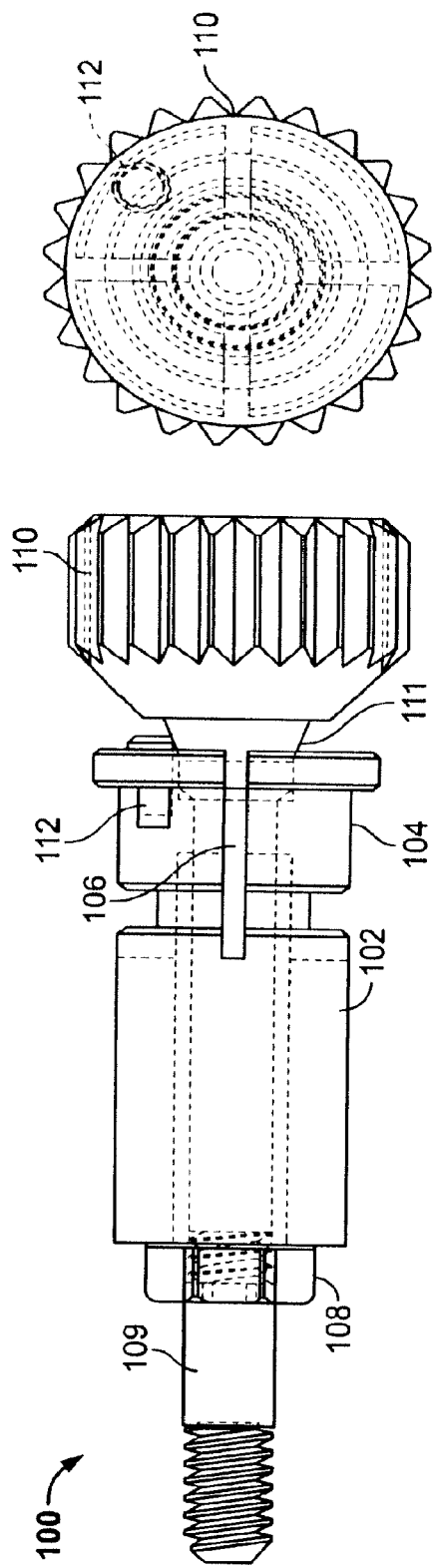
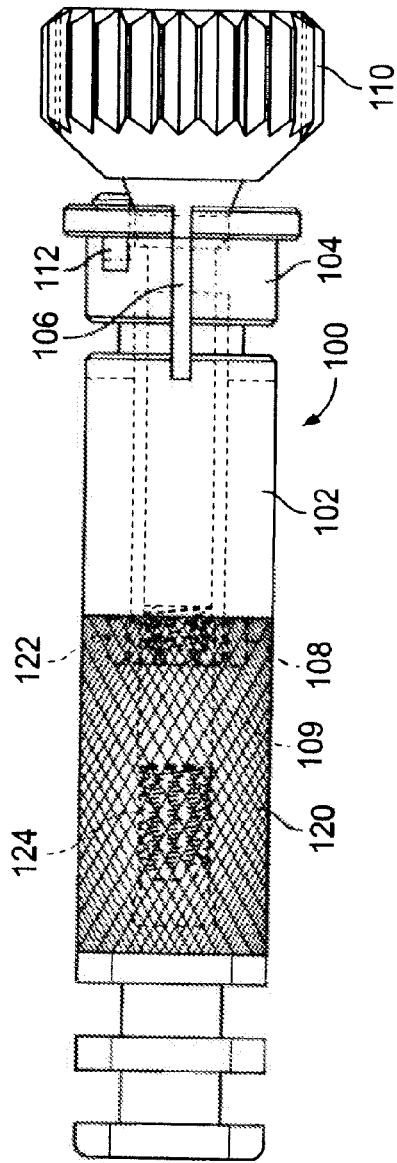
FIG. 5A
FIG. 5B
FIG. 6

METHOD OF CREATING AN ACCURATE BONE AND SOFT-TISSUE DIGITAL DENTAL MODEL

CROSS-REFERENCE TO RELATED APPLICATIONS

This application is a U.S. national stage of International Application No. PCT/US2009/040375, filed Apr. 13, 2009, which is related to and claims priority to U.S. Provisional Application No. 61/124,195, filed Apr. 15, 2008, each of which is hereby incorporated by reference herein in their entireties.

FIELD OF INVENTION

The present invention relates generally to dental implant systems. More particularly, the present invention relates to methods for creating and using accurate bone and soft-tissue digital dental models, surgical plans, and surgical guides.

BACKGROUND OF THE INVENTION

The dental restoration of a partially or wholly edentulous patient with artificial dentition is typically done in two stages. In the first stage, an incision is made through the gingiva to expose the underlying bone. After a series of drill bits creates an osteotomy in the bone, a dental implant is placed in the jawbone for osseointegration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant has the same general contour as the gingival portion of the natural tooth being replaced.

During the typical second stage of dental restoration, the healing abutment is removed and an impression coping is fitted onto the exposed end of the implant. This allows an impression of the specific region of the patient's mouth to be taken so that an artificial tooth is accurately constructed. After these processes, a dental laboratory creates a prosthesis to be permanently secured to the dental implant from the impression that was made.

In addition to the more traditional system for placing dental implants described above, some systems use guided placement of the dental implants. To do so, a surgical guide is placed in the patient's mouth at a known location. The surgical guide includes openings for providing the exact placement of drill bits used to create the osteotomy. Once the osteotomy is completed, the surgical guide may permit the dental implant to be placed through the same opening and enter the osteotomy that was guided by the surgical guide.

Surgical guides are typically created based on a dental scan (e.g., using a computed tomography ("CT") scanner) of the patient's mouth. A CT scanner provides the details of the patient's bone tissue, jawbone, and remaining teeth so that the surgical guide may be developed based on computer-aided design ("CAD") and computer-aided manufacturing ("CAM"). One example of the use of a CT scanner is disclosed in U.S. Patent Publication No. 2006/0093988 to Swaelens et al. ("Swaelens"), which is herein incorporated by reference in its entirety. Swaelens also describes the use of various tubes that may be placed within a surgical guide to receive the drill bits and implants. One example of the use of a CT-scan to develop a surgical plan involving a surgical guide is disclosed in U.S. Patent Application Ser. No. 61/003, 407, filed Nov. 16, 2007, and described in Biomet 3i's Navigator™ system product literature, "Navigator™ System For CT Guided Surgery Manual" that is publicly available, both of which are commonly owned and herein incorporated by reference in their entireties. Another example of the use of a CT-scan to develop a surgical plan is disclosed in U.S. Patent Publication No. 2006/0093988, which is herein incorporated by reference in its entirety.

CT scans tend to produce highly precise data for hard tissue (such as bone tissue or teeth) but produce less precise data for soft tissue (such as the gingival tissue). Thus, existing 3-D anatomic digital models and surgical guides typically do not accurately account for the gingival tissue overlying the patient's jawbone. Other techniques for acquiring gingival tissue data, such as using a barium sulfate-infused scanning appliance, are time and/or labor intensive and are often not particularly accurate.

Other methods are typically used to produce accurate soft tissue data. For example, soft tissue data may be acquired by taking an impression of the inside of a patient's mouth, using an intra-oral scanner, or the like. These methods, however, fail to provide accurate data relating to the hard tissue of the patient's mouth and, therefore, cannot be leveraged to improve the quality of the 3-D anatomic digital models and subsequent surgical guides created using these models.

When considering the dental and/or surgical plan for a specific patient, the maximum depth of the distal end of the dental implant within the bone is important so that the sinus cavity and mandibular canal may be avoided. Additionally, the location of the implant(s) relative to the gingival surface and underlying bone is important, especially one that involves the placement of several dental implants. Thus, it is important that precise data relating to both the hard tissue (e.g., bone structure and teeth) and the soft tissue (e.g., gingival tissue) of the patient's mouth is obtained and used to create a 3-D anatomic digital model from which the surgical guide may be developed.

Thus, there exists a need to develop an improved method for creating a highly accurate digital model that incorporates accurate data relating to both the hard tissue and the soft tissue of the patient's mouth and that forms an accurate basis from which to create a surgical model, a subsequent surgical guide, and/or custom abutments.

SUMMARY OF THE INVENTION

According to one process of the present invention, a method of creating a 3-D anatomic digital model for determining a desired location for placing at least one dental implant in a patient's mouth is disclosed. The method comprises the act of obtaining a first dataset associated with hard tissue of the patient's mouth. The method further comprises the act of obtaining a second dataset associated with soft tissue of the patient's mouth. The method further comprises the act of combining the first datasct and the second dataset to create a detailed structure of hard tissue and soft tissue having variable dimensions over the hard tissue.

According to another process of the present invention, a method for developing a surgical guide for guiding the insertion of at least one dental implant into a desired location in a patient's mouth is disclosed. The method comprises the act of obtaining a first dataset associated with hard tissue of the patient's mouth and a second dataset associated with soft tissue of the patient's mouth. The method further comprises the act of forming a 3-D anatomic digital model including the first dataset and the second dataset. The method further comprises the act of creating a surgical plan defined by the 3-D anatomic digital model. The surgical plan includes virtual implant positions. The method further comprises the act of scanning a cast model of the patient's mouth to obtain a third dataset. The method further comprises the act of combining the third dataset with the 3-D anatomic digital model. The method further comprises the act of placing at least one implant analog in the cast material in a location replicating the location of the at least one virtual implant in accord with the surgical plan. The method further comprises the act of attaching at least one implant-analog mount and at least one master tube into the cast model in accordance with the surgical plan to form a master cast. The method further comprises the act of pouring a flowable material over the master cast and around the at least one master tube. The method further comprises the act of allowing the flowable material to harden. The hardened material forms the surgical guide. The method further comprises the act of removing the at least one implant-analog mount and the surgical guide from the master cast.

According to another process of the present invention, a method of developing a surgical guide for guiding the insertion of at least one dental implant into a desired location in a patient's mouth is disclosed. The method comprises the act of scanning the inside of the patient's mouth to obtain a first dataset associated with bone tissue, teeth, or a combination thereof. The method further comprises the act of taking an impression of the patient's mouth. The method further comprises the act of scanning the impression to obtain a second dataset associated with a gingival surface. The method further comprises the act of merging the first dataset with the second dataset to form a 3-D anatomic digital model having gingival thickness data. The method further comprises the act of forming a cast model from the impression. The method further comprises the act of creating a surgical plan having virtual implants via the 3-D anatomic digital model, the virtual implants having location information associated therewith. The method further comprises the act of scanning the cast model to obtain a third dataset. The method further comprises the act of, using a robot, placing at least one implant analog in the cast model at a position dictated by the virtual implant location information.

According to another embodiment of the present invention, a method of developing a 3-D model of the patient's mouth is disclosed. The method comprises the act of scanning the inside of the patient's mouth to obtain a first dataset including data associated with the jawbone, bone tissue, teeth, or combinations thereof. The method further comprises the act of scanning the inside of the patient's mouth or an impression of the patient's mouth to obtain a second dataset including data associated with the gingival surface. The method further comprises the act of merging the first dataset with the second dataset to form a combined dataset. The method further comprises the act of removing overlapping data from the combined dataset to form a modified dataset. The method further comprises the act of adding soft tissue data associated with the region between the gingival surface and the jawbone to the combined dataset.

According to another process of the present invention, a method of placing a dental implant and prosthesis in a patient's mouth is disclosed. The method comprises the act of developing a 3-D anatomic digital model based on hard tissue data obtained from a computed tomography scan of the patient's mouth and soft tissue data obtained from an intra-oral scan or a dental impression of the patient's mouth. The method further comprises the act of developing a cast model of the patient's mouth. The method further comprises the act of scanning the cast model to obtain cast data. The method further comprises the act of merging the 3-D anatomic digital model with the cast data to obtain merged data. The method further comprises the act of developing a master cast by installing a dental implant analog to replicate a desired location of the dental implant into the cast model using the merged data. The method further comprises the act of developing on the master cast a surgical guide to be used in the placement of the dental implant in the patient's mouth. The surgical guide includes at least one opening generally adjacent to the dental implant analog. The method further comprises the act of placing the surgical guide in the patient's mouth. The method further comprises the act of installing the dental implant through the at least one opening in the surgical guide. The method further comprises the act of, after installing the dental implant, removing the surgical guide from the patient's mouth. The method further comprises the act of attaching a dental prosthesis to the dental implant.

The above summary of the present invention is not intended to represent each embodiment or every aspect of the present invention. This is the purpose of the figures and the detailed description which follow.

BRIEF DESCRIPTION OF THE DRAWINGS

FIGS. 5A-5B are side and top views of an implant-analog mount that may be used to develop the surgical guide;

FIG. 6 is a side view of the implant-analog mount in FIG. 5A-5B that is used with an implant analog;

Figure 1A:
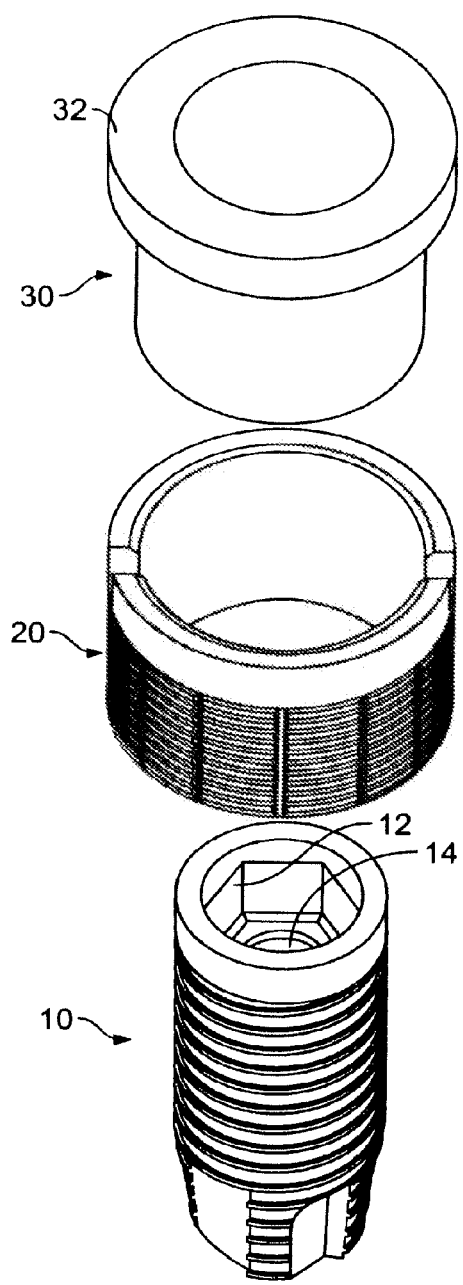
FIG. 1A illustrates an implant, a master tube for use in a surgical guide, and a guide tube for use with the master tube.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

The present invention is directed to methods for developing a single, highly accurate 3-D anatomic digital model that accurately accounts for both hard tissue data and soft tissue data. Such a model is required for computer-based surgical planning and an accurate surgical guide.

FIGS. 1-4 illustrate examples of implants, implant mounts, master tubes, and drill bits that may be used with a surgical guide formed according to embodiments of the present invention. FIGS. 5-6 illustrate implant analogs and implant-analog mounts that may be used to form the surgical guide. These components are also described in U.S. Provisional Patent Application Ser. No. 61/003,407, which is herein incorporated by reference in its entirety.

Figure 1B:
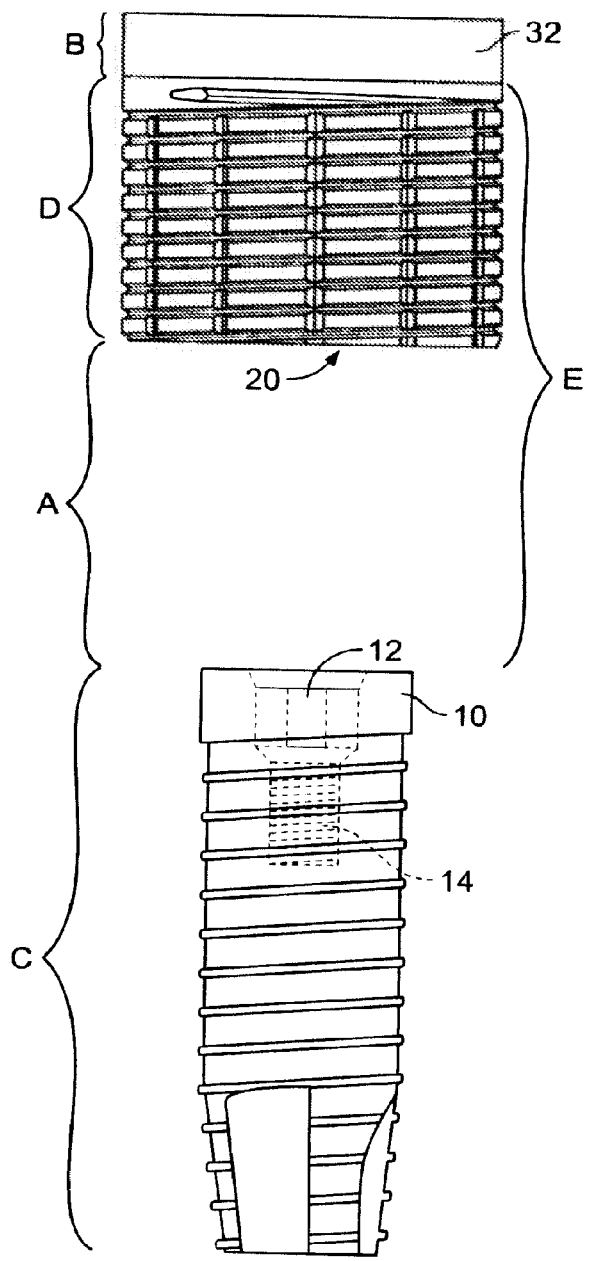
FIG. 1B schematically illustrates the various axially oriented dimensions of the components in FIG. 1A.

FIG. 1A illustrates some of the external components used for installing a dental implant 10 during dental surgery in a patient's mouth in accordance with a predetermined surgical plan. FIG. 1B illustrates the dimensions, which are discussed in more detail below, that are used to ensure the proper axial location of the dental implant 10 in the patient's bone. As shown, the implant 10 includes a non-rotational feature 12 in the form of a hexagonal socket and a threaded bore 14 located below the non-rotational feature 12. The non-rotational feature 12 may also have other internal forms, such as a different polygonal or non-round shape, and it may also be present in an external form, such as in a hexagonal (or other polygonal or non-round) boss that protrudes above the top surface of the implant 10. The external components include a master tube 20 that will be located within a surgical guide, which is discussed in more detail below, and a guide tube 30 having an upper lip 32. The guide tube 30 is like a bushing that fits snugly within the master tube 30 such that the upper lip 32 rests on the upper surface of the master tube 20.

With reference to FIG. 1B, to properly locate the implant 10 in the axial direction in accordance with the surgical plan, the length dimension "C" of the implant 10 must be known. Further, the dimension "A" is the distance from the seating surface of the implant 10 to the bottom of the master tube 20, which has a known length of dimension "D." Dimension "B" is the thickness of the lip 32 of the guide tube 30, which receives drill bits for drilling the osteotomy. Dimension "E" is the length dimension of an implant mount (e.g., implant mount 40 of FIGS. 2A-2C) and implant-analog mount (e.g., implant-analog mount 100 of FIG. 5A) that will be attached to the implant 10 and used to drive the implant 10 into the bone in accordance with the surgical plan. The surgical guide discussed below will have an axial dimension directly over each implant 10 that is greater than dimension "D" but less than dimension "E." This axial dimension of the surgical guide over the dental implant 10 will be chosen to ensure that the distance "E" is equal to one of several known and standard lengths for the implant mount 40 (e.g., 7.5 mm, 9 mm, 10.5 mm, 12 mm). In short, the dimensions "A," "B," "C," "D," and "E" of FIG. 1B are considered in developing the surgical guide that will place each dental implant 10 in accordance with the surgical plan.

Figure 2A:
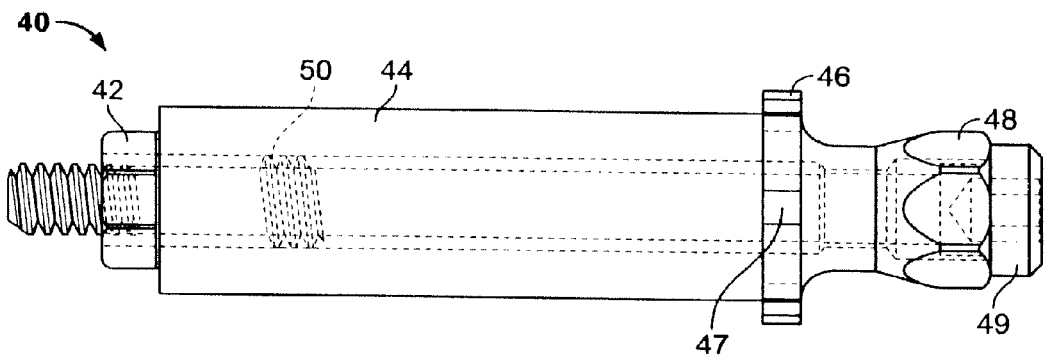
FIGS. 2A-2C are side, isometric, and top views of an implant mount for use in driving an implant into the osteotomy in the patient's mouth.
Figure 2B:
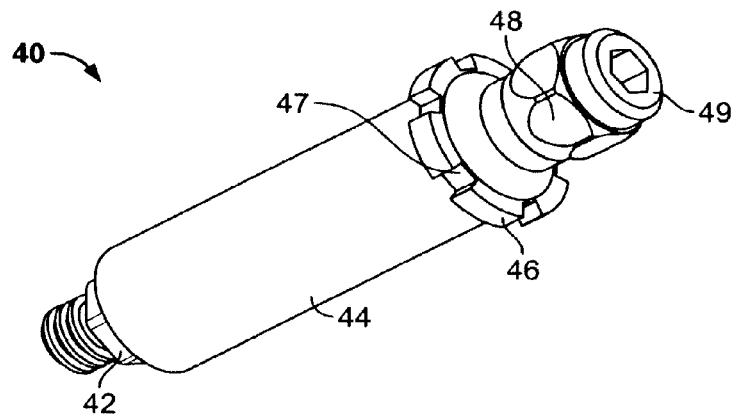
Figure 2C:
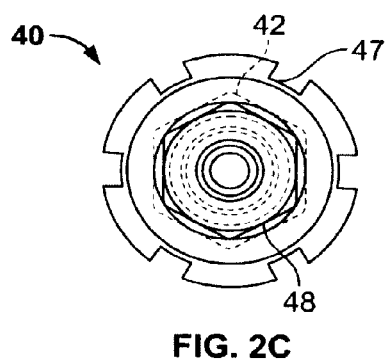

FIGS. 2A, 2B, and 2C illustrate one length of the implant mount 40 that may be used with the dental implant 10. Implant mounts are generally available in various lengths and diameters corresponding with various implant widths. The implant mount 40 includes a non-rotational feature 42 (as shown, a hexagonal boss) at one end of a main body 44 for mating with the non-rotational feature 12 of the implant 10. At the other end of the main body 44 is a flange 46 having a plurality of notches 47. A driving element 48 is located above the flange 46 for receiving torque from a manual or power drive to rotate the attached implant 10 into the bone of the patient. The implant mount 40 further includes a bore that receives a screw 49 extending through the entire implant mount 40. The bore may include internal threads 50 for capturing the threads of the screw 49 such that the screw 49 and the implant mount 40 are held together even when the implant mount 40 is unattached to a dental implant 10.

For visual alignment purposes, each notch 47 is aligned with one surface of the non-rotational feature 42 of the implant mount 40. In the illustrated embodiment, each notch 47 is also aligned with one surface of the driving element 48. Thus, the notches 47 help to identify the orientation of the underlying non-rotational feature 42. This is important because, once the implant 10 is installed in the patient's bone, the non-rotational feature 12 of the implant 10 must be at a known angular position in the patient's bone for a predefined prosthetic component (e.g., a bar, an abutment, etc.) to be aligned in the proper angular orientation when its non-rotational feature mates with the non-rotational feature 12 of the implant 10.

Figure 3:
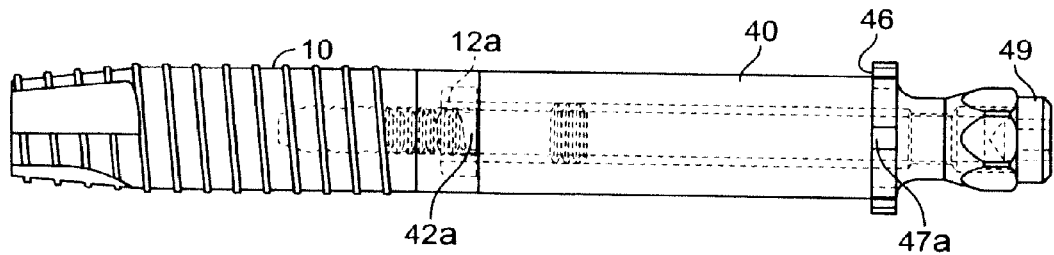
FIG. 3 illustrates the implant mount of FIGS. 2A-2C attached to the implant of FIGS. 1A-1B.

FIG. 3 illustrates the dental implant 10 attached to the implant mount 40 via the screw 49. Additionally, the non-rotational feature 12 of the implant 10 is coupled to the non-rotational feature 42 of the implant mount 40. Due to the position of the notches 47 on the flange 46, each notch 47a is aligned with corresponding surfaces 12a, 42a of the non-rotational features 12, 42. Accordingly, although a clinician cannot see the non-rotational feature 12 of the implant 10, the clinician still knows the angular orientation of the non-rotational feature 12 by inspecting the notches 47 on the implant mount 40.

Figure 4A:
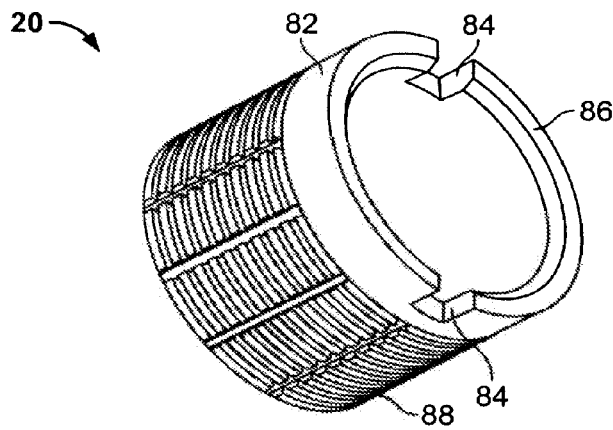
FIGS. 4A-4C are views of a master tube that may be placed in a surgical guide.
Figure 4B:
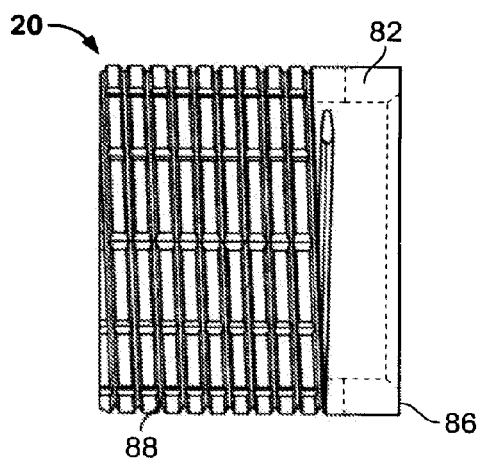
Figure 4C:
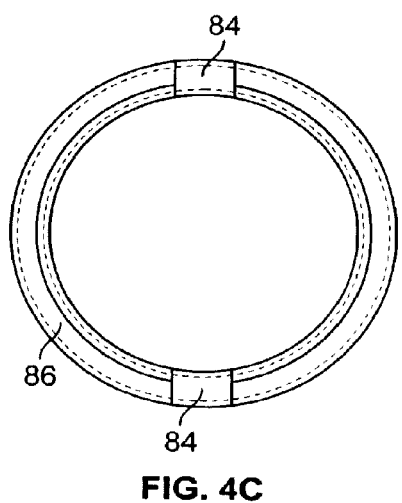

FIGS. 4A-4C illustrate the details of the master tube 20 according to one embodiment. The master tube 20 includes a main body 82 with notches 84 located on the upper surface 86. The master tube 20 includes a roughened side surface 88 that allows the master tube 20 to be better attached to the material of the surgical guide (e.g., surgical guide 390 of FIG. 14). As shown, the roughened surface 88 includes a spiral groove around the circumference of the main body 82 and axial grooves along the central axis of the main body 82 that intersect the spiral grooves. In other embodiments, the main body 82 may be a knurled surface or have any other surface structure that assists in fixing the master tube 20 within the material of the surgical guide.

The master tube 20 may come in different sizes to accommodate dental implants having different diameters. For example, a master tube 20 with an internal diameter of 4.1 mm may be used for implants 10 having diameters of 4.0 mm or smaller. Additionally, a master tube 20 with an internal diameter of 5.1 mm may be used for implants 10 having diameters between 4.0 mm and 5.0 mm.

According to one embodiment, a master tube may include a flange at the upper surface that allows the master tube to be axially retained in the surgical guide with better precision. The undersurface of the flange engages the material of the surgical guide, so as to resist any axial movement of the master tube relative to the surgical guide. The flange may rest on the top surface of the surgical guide or within a counter-bored opening within the top surface of the surgical guide. In either case, the dimensions "A," "B," "C," "D," and "E" of FIG. 1B are also applicable to the master tube so as to develop a surgical guide that will place each dental implant 10 in accordance with the surgical plan.

FIGS. 5A-5B illustrate an implant-analog mount 100, according to one embodiment, that may be used to assist in developing the surgical guide. The implant-analog mount 100 includes a main body 102 and an expandable top section 104, which includes a plurality of slots 106. The lower end of the main body 102 includes a non-rotational feature 108 (e.g., a hexagonal boss) that will engage a corresponding mating surface in the implant analog. The implant-analog mount 100 includes a screw 109 with a large rotatable head 110. When the rotatable head 110 is tightened such that the screw 109 is tightened into the implant analog, further rotation causes the tapered section 111 of the screw 109 to force the expandable top section 104 outward.

An orientation pin 112 is located on the expandable top section 104 and is aligned with one of the flat surfaces on the non-rotational feature 108. The orientation pin 112 extends below the top flange of the expandable top section 104 and, as described below, mates with the notch 84 within the master tube 20 when developing the master cast described below.

FIG. 6 illustrates the implant-analog mount 100 attached to an implant analog 120, which will also be used to assist in forming the surgical guide. The implant analog 120 has an upper surface that replicates the upper surface of the dental implant 10. Thus, the implant analog 120 includes a non-rotation feature 122 that mates with the non-rotational feature 108 of the implant-analog mount 100. When doing so, the orientation marker 112 is then aligned with the non-rotation feature 122 of the implant analog 120. The implant analog 120 also includes internal threads 124 for receiving the screw 109 to hold the implant analog 120 to the implant-analog mount 100.

According to the embodiments of the present invention, a 3-D anatomic digital model for a patient may be developed by merging (1) data obtained by scanning the patient's mouth with a CT scanner (or other suitable scanning technologies or devices) to obtain data associated with the bone structure, teeth, and/or pre-placed physical markers (e.g., in the case of a fully edentulous patient, described in more detail below) with (2) data obtained by taking an impression of the patient's mouth and scanning the impression or by scanning the inside of the patient's mouth with an intra-oral scanner to obtain data associated with the gingival surface. A surgical plan, created using this 3-D anatomic digital model in conjunction with planning software, is then used to precisely place an implant analog(s) into a cast of the patient's pre-surgical anatomic scenario in a position replicating a desired position of the dental implant to be inserted into the patient's mouth, thereby creating a master cast. The master cast is then used to create a surgical guide.

The remainder of the detailed description will assume that the patient is edentulous and that the surgical guide is resting on the soft tissue (e.g., the gingival surface). For fully edentulous patients, a hard tissue reference common to both the hard tissue dataset and the soft tissue dataset is required for shape matching, as this hard tissue reference will be the only data common to both the hard tissue dataset and the soft tissue dataset. Thus, a physical marker may be placed in the patient's mouth as a reference point. The marker may include a bone pin, a fixation screw, or the like. It should be understood, however, that the embodiments of the present invention may also be used with partially edentulous patients.

Figure 7A:
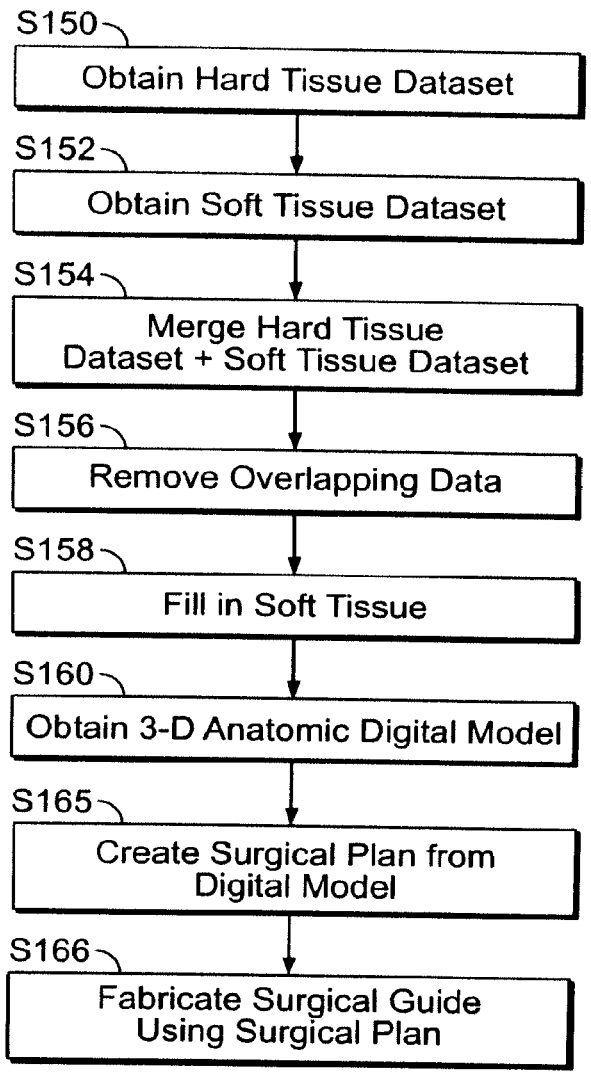
FIG. 7A is a flow diagram detailing a method of forming a surgical plan according to one process.

Referring to FIG. 7A, a method of creating a surgical plan according to one process is illustrated. To create the surgical plan, three-dimensional ("3-D") data relating to a patient's hard tissue is obtained using a dental scan such as a CT scan or other suitable scanning technologies or devices at step s150. Specifically, the CT scanner digitizes data relating to the patient's bone structure (e.g., jawbone) and teeth to create a hard tissue dataset. The hard tissue dataset includes accurate hard tissue data.

At step s152, a 3-D soft tissue dataset is acquired. According to one embodiment, an impression (e.g., impression 310 of FIG. 9) is taken of the patient's gingival surface and teeth (if any) using common techniques involving the use of impression material within the patient's mouth. The impression is then scanned and digitized to obtain the soft tissue dataset. Alternatively, a stone cast of the patient's mouth is formed, and the stone cast is scanned and digitized. One suitable type of scanner is the 3D Scanner D-250™ manufactured by 3Shape A/S (Copenhagen, Denmark) ("3Shape Scanner"). In another embodiment, the soft tissue dataset is obtained by scanning the inside of the patient's mouth using an intra-oral scanner.

The resulting soft tissue dataset obtained at step s152 includes very accurate data of the outer surface of a patient's dentition. The soft tissue dataset is a digitized surface of zero thickness and represents the outer surface of the teeth and gingival tissue. Although in the process of FIG. 7A, the soft tissue dataset is obtained after obtaining the hard tissue dataset, it is also contemplated that the soft tissue dataset may be obtained prior to obtaining the hard tissue dataset.

At step s154, a shape-matching algorithm is applied to merge the hard tissue dataset and the soft tissue dataset. The shape-matching algorithm utilizes features common to both datasets, such as the outer surface of the dentition, pre-placed physical markers, existing teeth, or the like, to merge the two datasets. Overlapping data common to both the soft tissue dataset and the hard tissue dataset (e.g., data associated with the dentition) is removed from the hard tissue dataset at step s156. In another embodiment, common data is removed from the soft tissue dataset. The region between the resulting merged dataset and the jawbone leaves a "gap," which corresponds with the thickness of the gingival tissue. This gap is then filled in with soft tissue within the model at step s158. A resulting 3-D anatomic digital model is then obtained at step s160. A surgical plan may be created from the digital model at step s165. A surgical guide may be fabricated using the surgical plan at step s166.

Figure 7B:
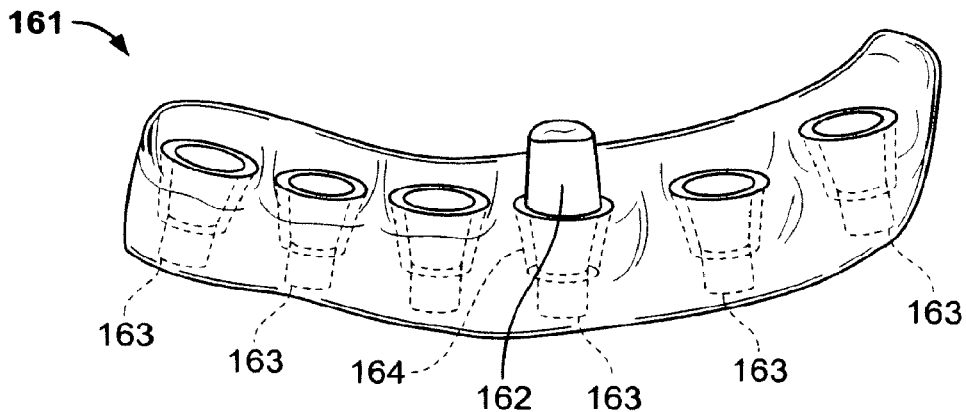
FIG. 7B is a 3D computer model (a virtual model) of a portion of a patient's mouth.

The surgical plan may be created using the 3-D anatomic digital model and planning software. The surgical plan includes information regarding the location, position, orientation, and size of virtual implants based on the conditions of the patient's mouth. FIG. 7B illustrates a 3-D CAD model 161

(on a computer display) of a virtual custom abutment 162 and virtual implant analogs 163 utilizing the 3-D anatomic digital model obtained at step s160. An opening 164 in the CAD model 161 is tapered as it leads towards the virtual implant analog 163. This tapering is chosen by the operator of the CAD model 161 after consideration of the location of the underlying dental implant that has been dictated by the cast model and the location of the adjacent teeth, if any. Further, the tapering is dictated by the size and shape of the virtual custom abutment 162 that has been designed by the operator. Although the opening 164 has been illustrated having a straight-wall taper, the opening 164 may have a curved-wall taper. Further, the opening 164 at its terminal and may be circular, elliptical, or have other non-circular shapes as dictated by the virtual custom abutment 142 and the three-dimensional "saddle" shape of the gingival tissue between adjacent teeth. This opening 164 may be created by a robot manipulator or an alternative robot 358 discussed with reference to FIGS. 10A-D.

Figure 8:
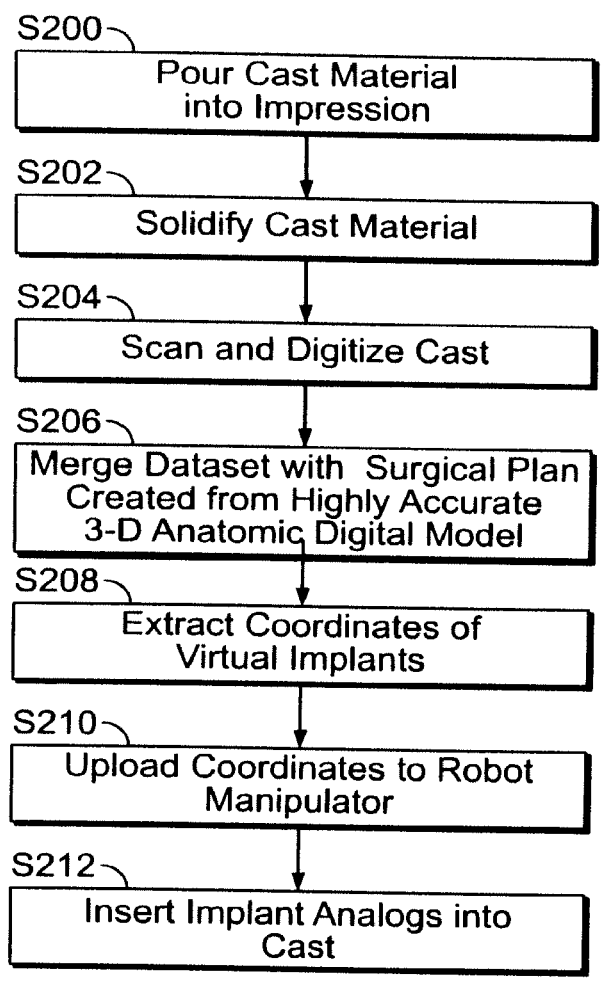
FIG. 8 is a flow diagram detailing a method of forming a master cast using the surgical plan of FIGS. 7A-7B according to one process.
Figure 14:
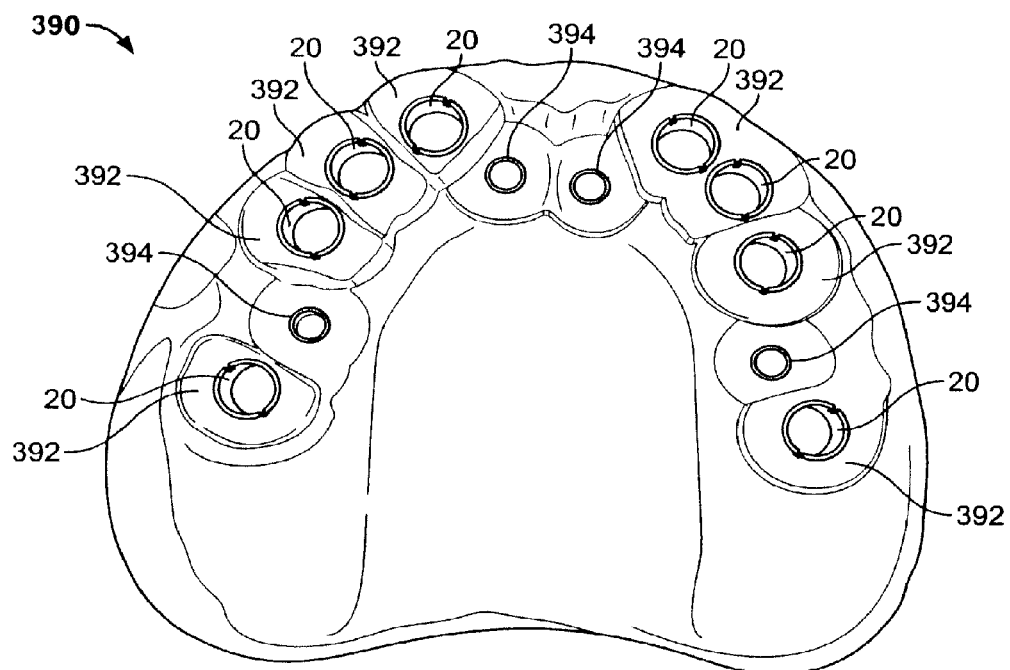
FIG. 14 is a top view of a surgical guide that may be used in a patient's mouth to guide the placement of eight dental implants.

The resulting surgical plan may be used to create a master cast, which may then be used to fabricate a surgical guide (e.g., surgical guide 390 of FIG. 14). The method of forming the master cast according to one process is shown in FIG. 8. At step s200, a flowable cast material is poured into an impression of the gingival surface. The impression used in step s200 may be the impression obtained during the process of acquiring the soft tissue dataset described above (e.g., during step s152 of FIG. 7A). It is contemplated that another or a new impression may also be used during step s200. For example, a new impression may be used if an intra-oral scanner was used during step s152 of FIG. 7A to acquire the soft tissue dataset.

Figure 9:
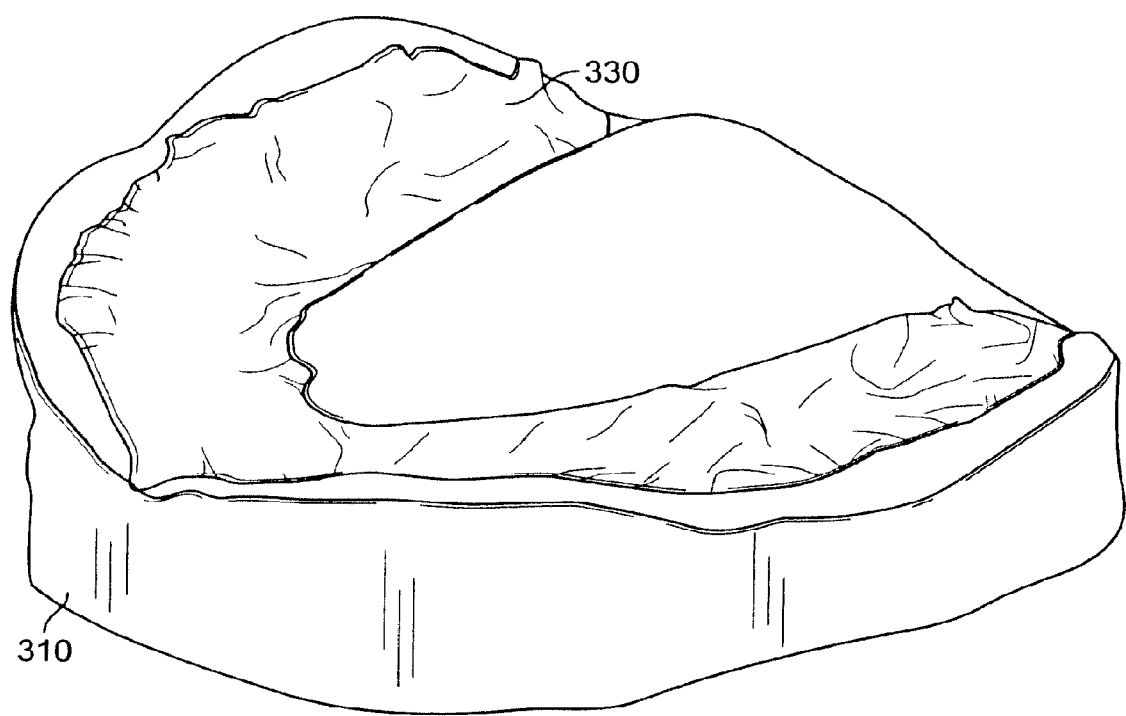
FIG. 9 illustrates flowable cast material being poured into an impression of a patient's gingival surface to develop a cast model of the patient's mandible.

Before discussing the remaining steps of FIG. 8, attention will be given to FIGS. 9-10. FIG. 9 illustrates one example of a method for developing a cast model of the patient's mandible. FIGS. 10A-D show schematic representations of a robot manipulator system configured to place an implant analog into the cast model of FIG. 9, according to one embodiment.

FIG. 9 illustrates the making of a cast model using a dental impression 310. In the illustration of FIG. 9, flowable cast material 330 is poured into the impression 310, which has a contour that is the negative impression of the patient's gingival surface. The cast material 330 may include stone or other suitable material. The cast material 330 is then allowed to solidify at step s202. It should be noted that the skilled artisan will recognize that there are many ways to make a cast. For example, various materials may be used.

Referring also to FIGS. 10A-E, after the cast material 330 has solidified at step s202, a resulting cast model 350 is mounted on a base structure (e.g., a male base structure 368). The relative position and/or coordinates of implant analogs 120 to be placed in the cast model 350 may be generated using the coordinate system within a 3-D CAD model. The position of the implant analogs replicate the desired location, position, and orientation of the virtual implants to be placed into the patient's mouth. This desired location, position, and orientation of the virtual implants was determined by the surgical plan. A common work structure (e.g., female work structure 369) associated with the robot may be used in scanning the cast model 350 and in placing the implant analogs 120 using a robot manipulator 358. It is contemplated that types of base structures other than those shown in FIGS. 10A-D may also be used. For example, in some embodiments, the cast model 350 may be mounted on a female base structure and the common base structure may be a male base structure. In other embodiments, the scanner and the robot manipulator do not share a common base structure.

Figure 10A:
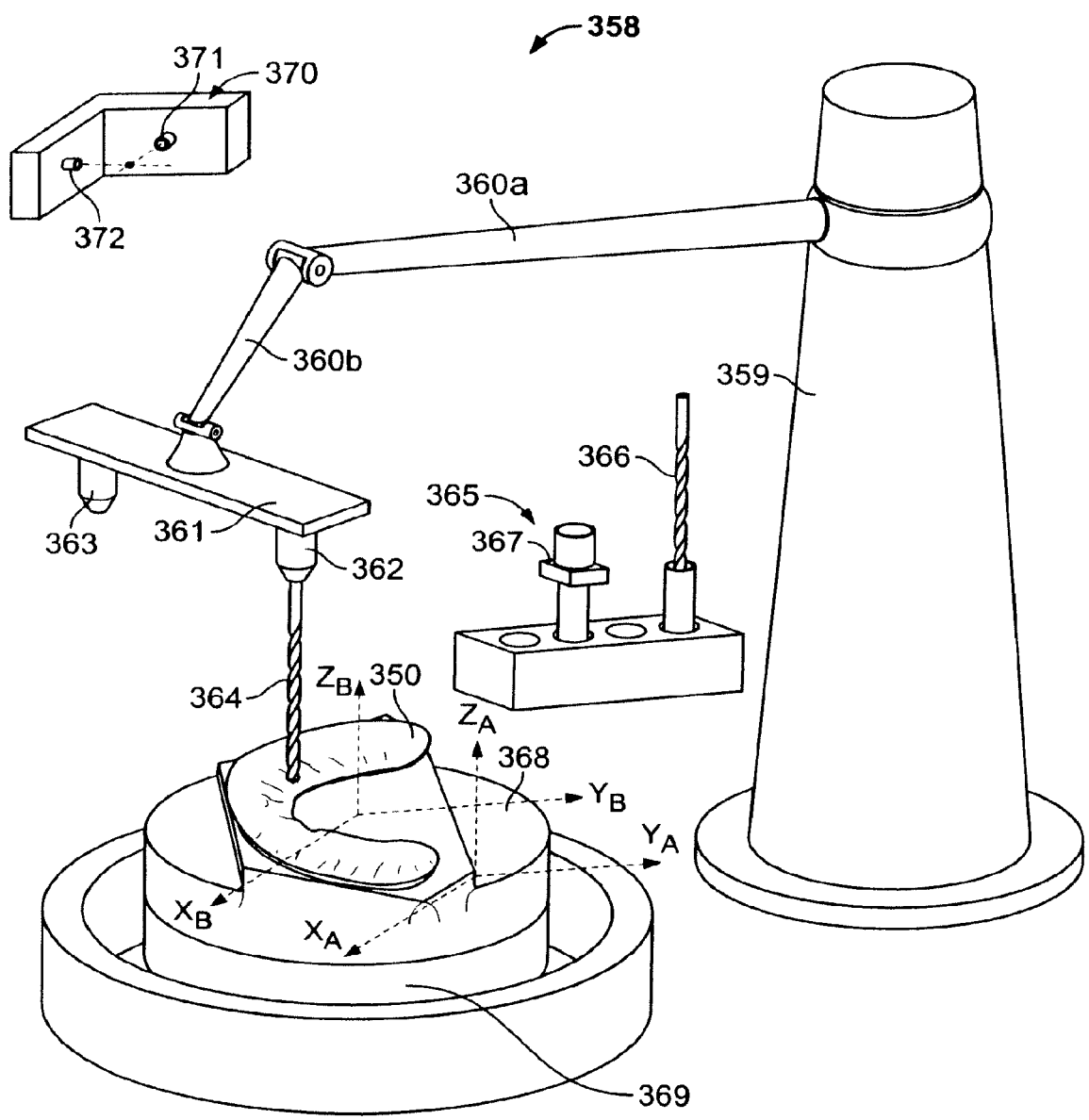
FIG. 10A illustrates a robot that may be used to modify the cast model of FIG. 9.

The male base structure 368 is then attached to the work structure 369, as shown in FIG. 10A, and scanned using the 3Shape Scanner (or other suitable scanning device) at step s204. In one embodiment, the scanner measures X, Y, and Z positions of one or more features of the cast model 350 relative to the axes on the base structure 368, also referred to as the base structure origin, thereby acquiring a digitized cast dataset of the cast model 350. Thus, when the base structure 368 is in a known position with respect to the work structure 369, an exact desired location for an implant analog 120 may be determined. In another embodiment, a 3Sphere reference is used to create a common coordinate system. In this embodiment, a scanner scans a calibration standard with three spheres thereon. A robot then probes these three spheres. Using the scan and probe data, a common coordinate system is established between the robot and the scanner.

Referring back to FIG. 8, the digitized cast dataset is then merged with the previously-obtained 3-D anatomic digital model from which the surgical plan was created (see FIG. 7A) using a second shape-matching algorithm at step s206. The second shape-matching algorithm may be the same as or different from the shape-matching algorithm used to merge the hard tissue dataset and the soft tissue dataset at step s154 of FIG. 7A to obtain the 3-D anatomic digital model. The coordinates of the virtual implant(s) to be inserted into the patient's mouth and, thus, the coordinates of the corresponding implant analogs 120 relative to the base structure coordinate system, are then extracted at step s208.

The coordinates of the virtual implants are uploaded to the robot manipulator 358 at step s210. At step s212, the robot manipulator 358 inserts the implant analogs 120 into the cast model 350 (see FIG. 10D) in an installation site corresponding with the location, position, and orientation of the virtual implants. The robot manipulator 358 is able to accurately place the implant analog 120 in the cast model 350 such that the position of the implant analog 120 within the cast model 350 is substantially identical to the position of the virtual implant determined by the surgical plan. Because in the illustrated embodiment, there is a need for eight implants 10, eight implant analogs 120 are inserted into the cast model 350. In one embodiment, the robot manipulator 358 uses the relative position information to place an implant analog 120 into a securing material, such as an epoxy, located on the cast model 350.

FIG. 10A illustrates one example of a simple schematic construction for the robot 358. The skilled artisan would appreciate that numerous types of robots are available having various control features, motors, and manipulating arms and tools. For example, the robot 358 may be an Epson PS5 six-axis robot with an Epson RC520 controller (Seiko Epson Corporation, Japan). The robot 358 in FIGS. 10A-D performs various functions related to modifying the cast model 350 and placing the actual implant analog 120. In particular, as will be described in more detail below, the robot 358 modifies the cast model 350 after it has solidified to create an actual opening that is substantially similar to the virtual opening 164. The position in which to place the implant analogs is determined by the surgical plan. The associated virtual openings are required to accommodate the analogs. Further, the robot 358 places an implant analog 120 in substantially the same position and with substantially the same orientation as the virtual implant analogs 163 of FIG. 7B.

The robot 358 includes a base structure 359 that is supported on a table or other work bench. The base structure 359 typically has one or more moving arms 360a,b having a terminal structure 361 for supporting one or more tool holders 362, 363 that grip and/or manipulate tools or other components. As shown, the base structure 359 includes an arm 360 having multiple pivotable sections 360a and 360b, and the tool holder 362 includes a drill bit 364. The terminal structure 361, the arm 360, the base structure 359, and/or the tool holders 362, 363 include gears and other common components for transmitting rotational energy to a tool (e.g., the drill bit 364) being held by one of the tool holders 362, 363.

The arm 360 (and, thus, the terminal structure 361) may be moved in all directions relative to the cast model 350 and a pallet 365. The pallet 365 includes a specific sequence of tools or other components that are placed within the pallet 365 prior to the operation of the robot 358. As shown, the pallet 365 includes an additional drill bit 366 at one location and an implant analog holder 367 at a second location. Typically, after the data from the 3-D CAD model 161 of FIG. 7B is transferred to the control system for the robot 358, the operator of the robot 358 will be instructed to provide a certain sequence of tools or other components in the pallet 365 to accommodate the development of the particular opening and the placement of the particular implant analog 120 for the case.

In FIG. 10A, the cast model 350 is directly coupled to a base structure 368 that is the same base structure that was used for scanning the cast model 350 at step s204 of FIG. 8. As such, the base structure 368 is used in both the scanning of the cast model 350 and in the later modification of the cast model 350 by the robot 358. The base structure 368 includes alignment features and magnetic features for precision mating with corresponding structures on the work structure 369 associated with the robot 358. The work structure 369 is at a known location relative to the base structure 359 such that any tool or other component within the tool holders 362, 363 can be accurately positioned relative to the work structure 369.

To help arrange for the precision location of the tool 364 relative to the cast model 350, the cast model 350 (and its base structure 368) has an analog coordinate system, which is labeled as $X_A$, $Y_A$, $Z_A$, for locating the custom abutment, which will ultimately fit on the implant analog to be located within the opening in the cast model 350. If desired, a custom abutment may be designed with respect to the analog coordinate system. Further, the robot 358 (and the scanning system previously used) has its own base coordinate system, which is labeled as $X_B$, $Y_B$, $Z_B$.

When the data from the 3-D CAD model 161 is transferred to the control system for the robot 358, the data includes at least two types of data sets. A first data set indicates the type of implant analog that will be used in the cast model 350. A second data set indicates the relative location of the analog coordinate system to the base coordinate system so that the creation of the hole in the cast model 350 and the placement of the implant analog is substantially identical to that which has been virtually modeled. Optionally, a third data set may define the gingival margin of the custom abutment 162 so that a properly sized opening may be created above the implant analog, allowing the custom abutment to fit properly within the cast model. This optional third data set may be helpful because the actual custom abutment is larger in diameter than the implant analog such that the opening must be contoured in a tapered fashion (e.g., straight-wall taper, curved wall taper, etc.) to accommodate the actual custom abutment.

The robot 358 of FIG. 10A may also include a calibration mechanism 370 such that the tool (e.g., the tip end of drill bit 364) is placed at a known location or "zeroed" before developing the opening and/or placement of the implant analog. As shown, the calibration system 370 includes two intersecting lasers (e.g., HeNe lasers) 371, 372. Prior to any work on the cast model 350, the tool 364 is placed at the intersection of the two lasers 371, 372 to insure accuracy of the tool 364 within the base coordinate system ($X_B$, $Y_B$, $Z_B$). The operator can slightly adjust the tool 364 to place it at the intersection of the two lasers 371, 372, assuming the calibration system 370 indicates that an adjustment is needed or if the operator may visualize that an adjustment is needed.

Figure 10B:
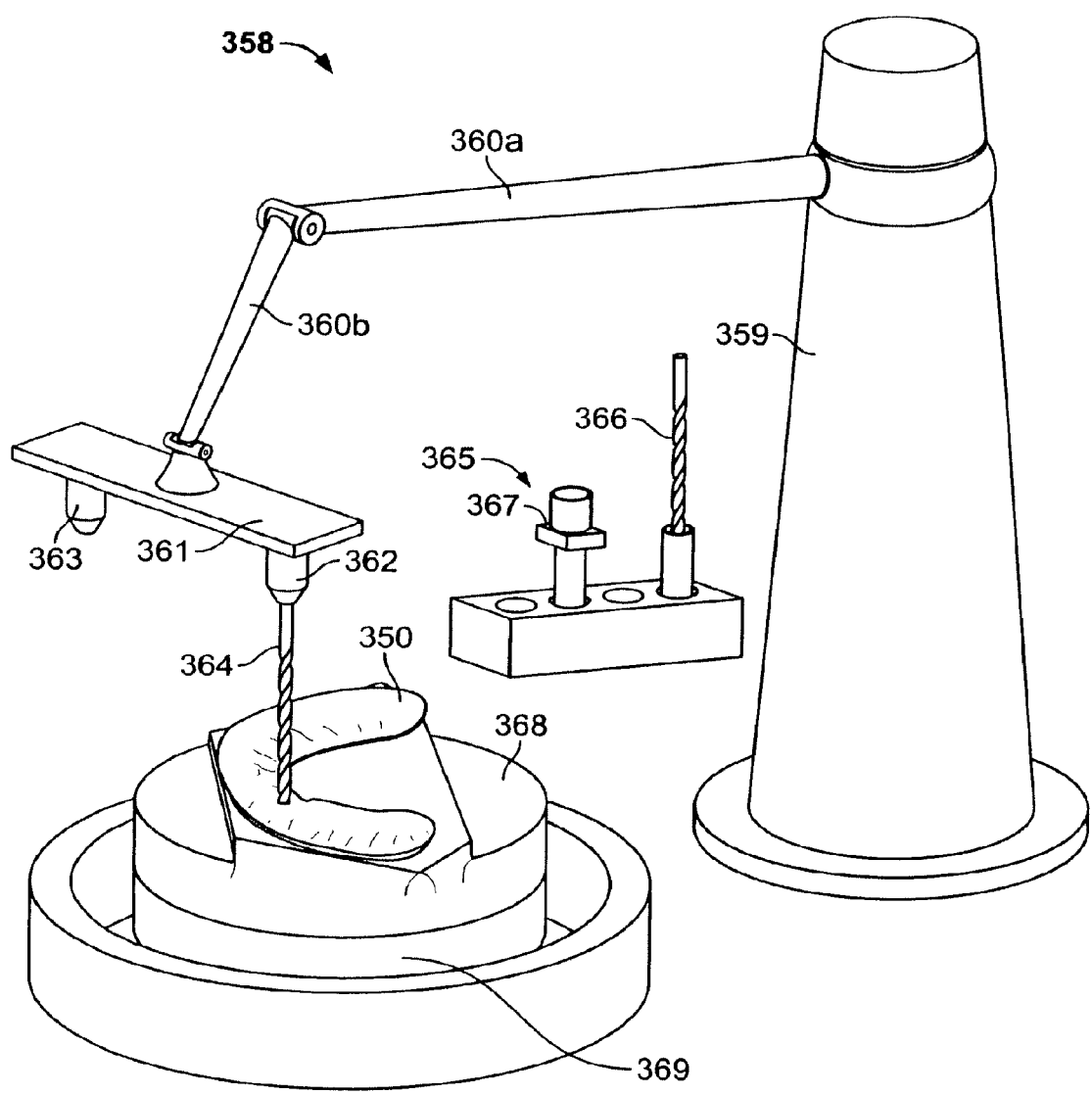
FIG. 10B illustrates the robot of FIG. 10A as it creates an opening in the cast model.

In FIG. 10B, the drill bit 364 has been moved by the robot 358 to begin the development of the opening in the cast model 350. The drill bit 364 creates the contoured pocket of the opening (as dictated by the tapered opening 164 in FIG. 7B). The drill bit 364 has a smaller diameter than any portion of the opening such that it is used as a milling tool to create the contoured pocket. In one embodiment, the drill bit 364 then creates the lower portion of the opening that will receive the implant analog 120. In doing so, the drill bit 364 of the robot 358 creates a bottom wall to the opening that is located at a position within the cast model 350 that will cause the particular implant analog for that case to have its upper mating surface (see FIG. 10E) at a location that is substantially identical to the location of the virtual implant. In another embodiment, the hole for the analog (the "analog pocket") is oversized relative to the analog in all dimensions. The robot 358 then holds the analog in space within the confines of the analog pocket while the adhesive bonds the analog to the cast model 350.

Figure 10C:
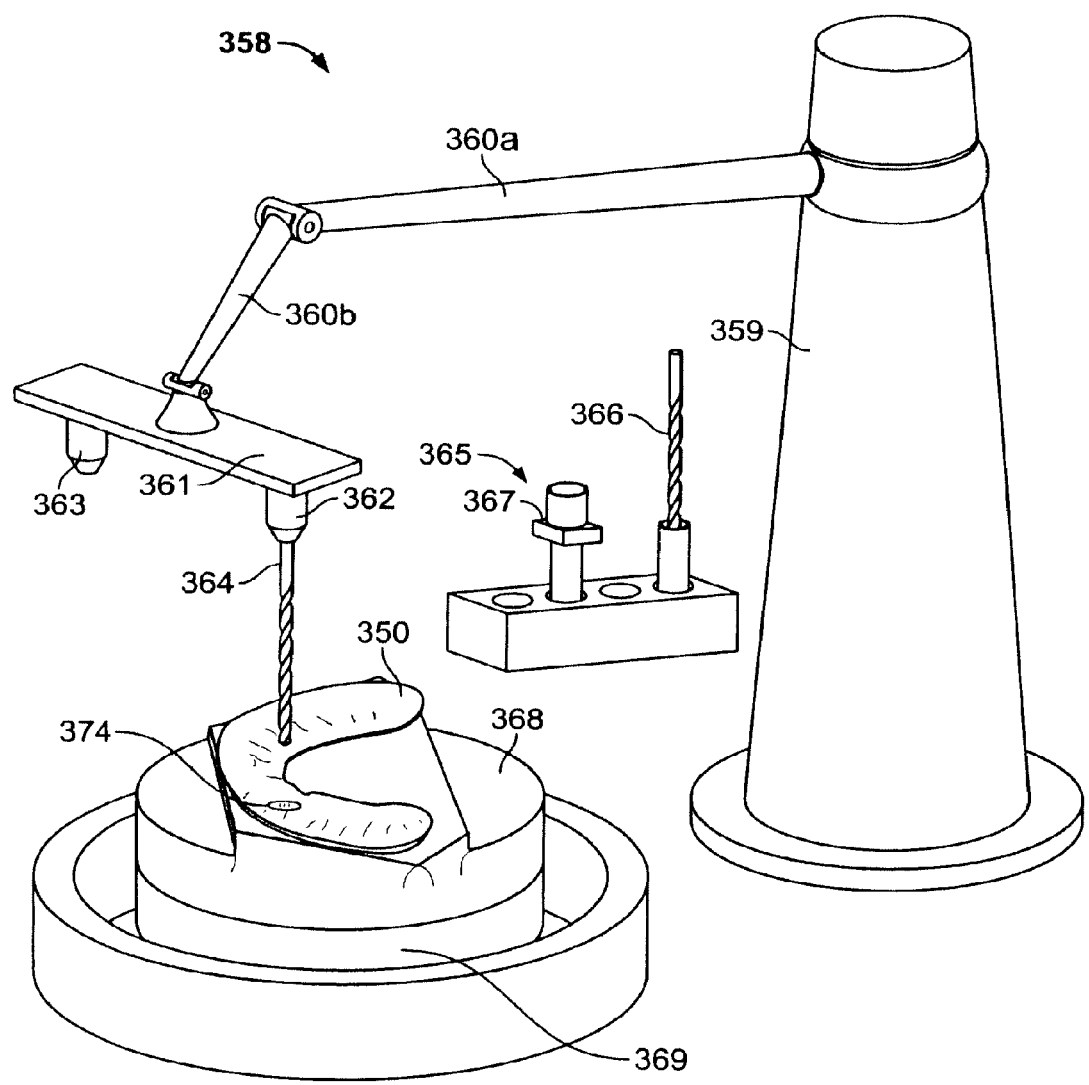
FIG. 10C illustrates the robot of FIG. 10A after it has created an opening in the cast model.

FIG. 10C illustrates the end result of an opening 374 that was created in the cast model 350 by the robot 358. While the development of the opening 374 has been described by the use of a single drill bit 364, it should be understood that the robot 358 can utilize multiple tools (e.g., a second drill bit 366 in the pallet 365, or a more traditional milling tool) to create the opening 374. Further, because multiple virtual implants are required in the illustrated embodiment, the robot 358 is required to create multiple openings 374, each of which uses multiple tools from the pallet 365. The use of multiple tools may require a calibration by the calibration system 370 (FIG. 10A) prior to the use of each tool.

Figure 10D:
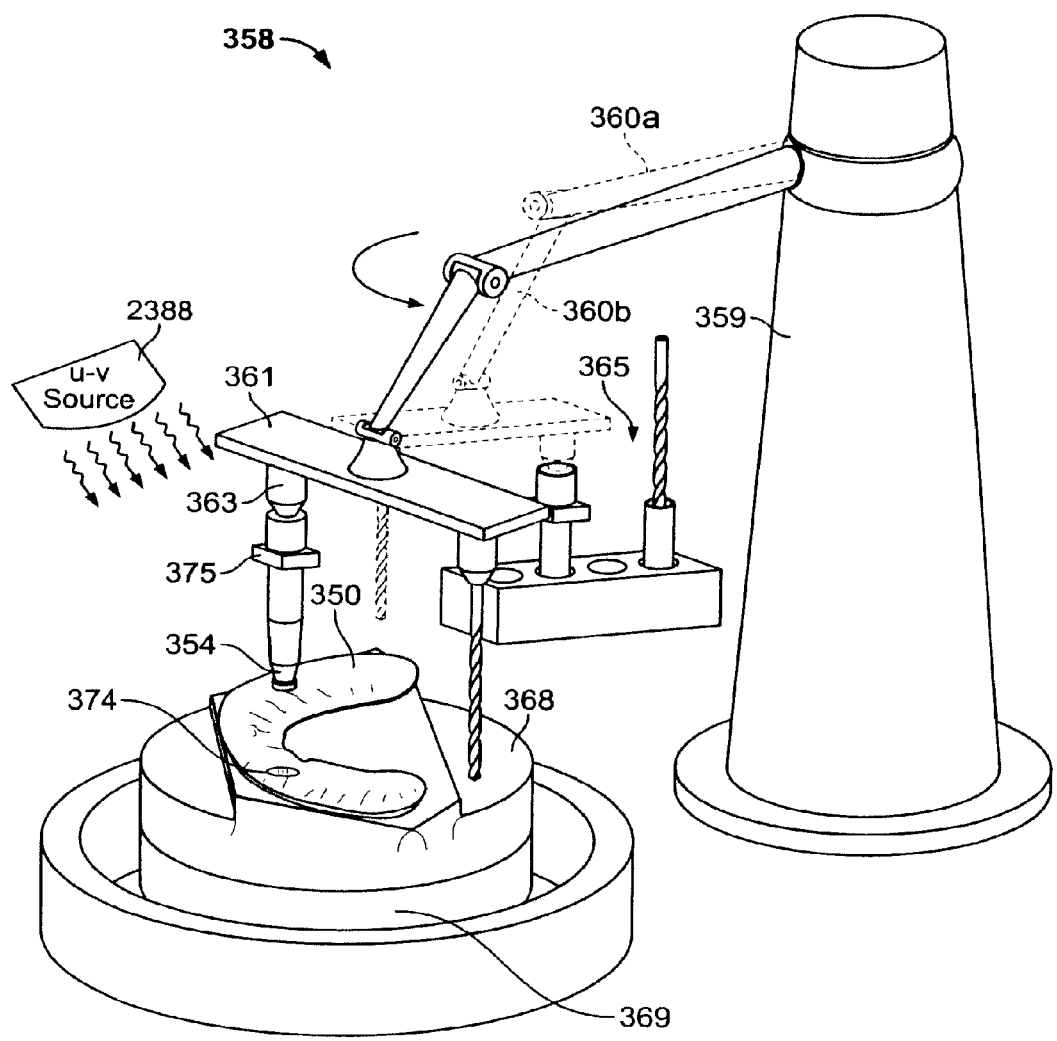
FIG. 10D illustrates the robot of FIG. 10A placing an implant analog in the cast model.

FIG. 10D illustrates the movement of the robot 358 to grip an implant analog holder 375 from the pallet 365 by use of the tool holder 363 for placement of the implant analog 120. Once the opening 374 has been completed, the operator will remove all remaining particles and debris from the drilling process from the cast model 350. An adhesive is placed within the opening 374 and also placed (e.g., manually brushed) on the terminal end of the implant analog 120. Alternatively, an adhesive activator agent is placed on the implant analog 120 to accelerate the curing process. It should be understood, however, that the work station for the robot 358 may have bins of adhesive (and activator agents) such that the robot 358 "dips" the end of the implant analog 120 into one or more of these bins without manual operator intervention.

After calibrating the location of the implant analog 120 with the calibration system 370 (FIG. 10A), the robot 358 then moves the implant analog holder 375 in such a manner so as to place the implant analog 120 at the bottom of the opening 374. In doing so, the orientation of the anti-rotational feature of the implant analog 120 is critical such that it matches the orientation of the anti-rotational feature of the implant in the patient's mouth (i.e., all six degrees of freedom are constrained in the same manner as the implant that is located in the patient's mouth). When the robot 358 has finished placement of the implant analog 120 within the opening 374, an energy source (e.g., UV light source) is used to quickly cure the adhesive such that the implant analog 120 is physically constrained and attached to the cast model 350 within the opening 374. Preferably, the adhesive is a UV-curable adhesive.

Figure 10E:
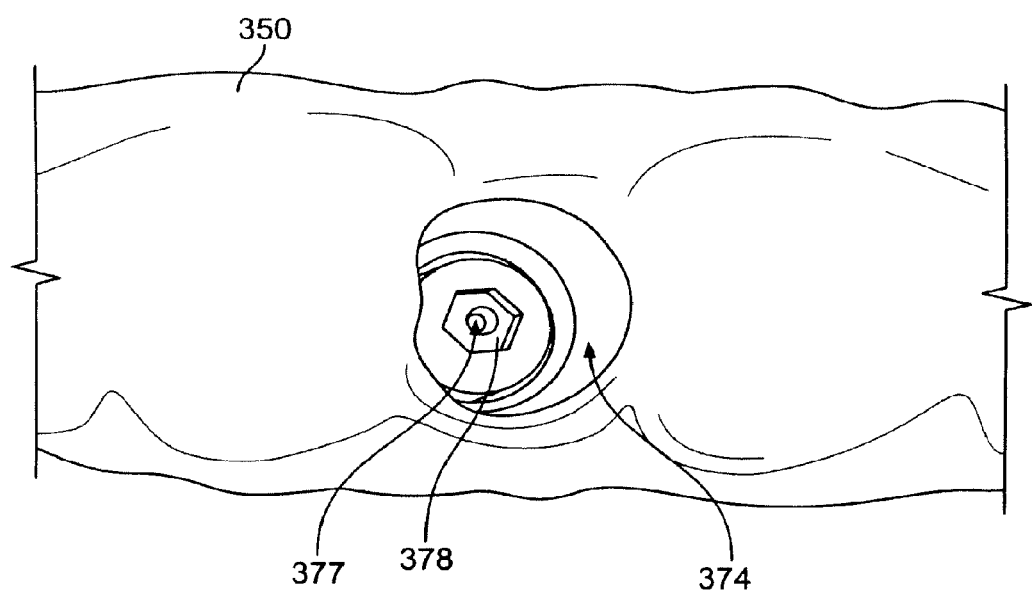
FIG. 10E illustrates the details of the opening of the cast model after the robot of FIG. 10A has placed the implant analog therein.

Once the adhesive has cured, the robot 358 commands the gripping mechanism of the tool holder 363 to release the implant analog holder 375. The implant analog holder 375 is held to the implant analog 120 through a long screw. Thus, the operator removes the long screw such that the implant analog 120 remains by itself within the opening 374 (attached via the adhesive), as is shown in FIG. 10E. In particular, the implant analog 120 and its threaded bore 377 and anti-rotational feature 378, are located at a specific position and orientation within the opening 374. It should be understood that the robot 358 may also include the necessary tools (e.g. screwdriver tip) in the pallet 368 to release the implant analog holder 375 from the implant analog 120 so that operator intervention is not required.

Figure 11:
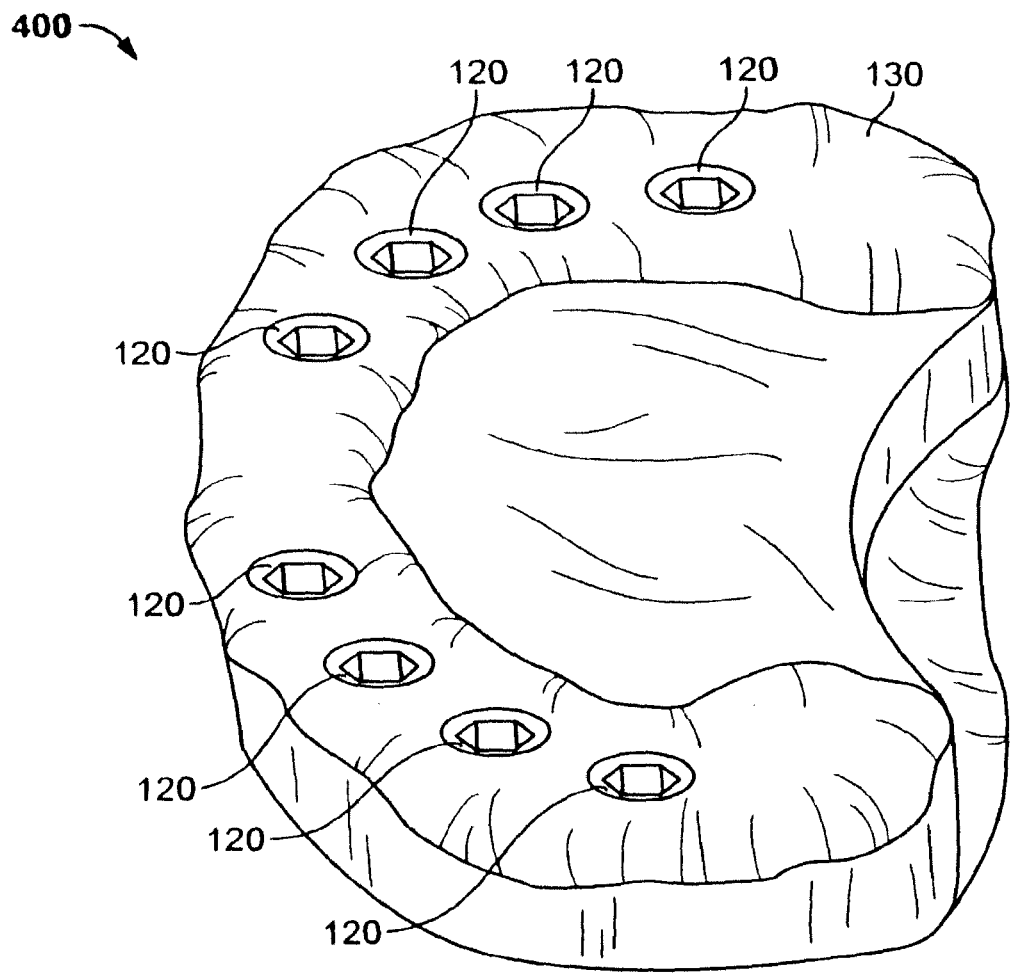
FIG. 11 illustrates a master cast formed using the process of FIGS. 8 and 10, according to one embodiment.

FIG. 11 illustrates a resulting master cast 400 once multiple implant analogs have been inserted via the robot 358 of FIGS. 10A-D. The master cast 400 includes the eight implants analogs 120 that will replicate the positions of the eight dental implants 10 that will be inserted into the patient's bone by use of the surgical guide.

Figure 12:
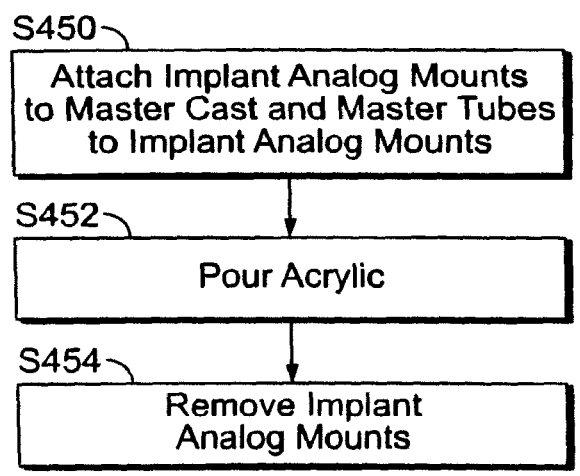
FIG. 12 is a flow diagram detailing a method of forming a surgical guide according to one process.
Figure 13A:
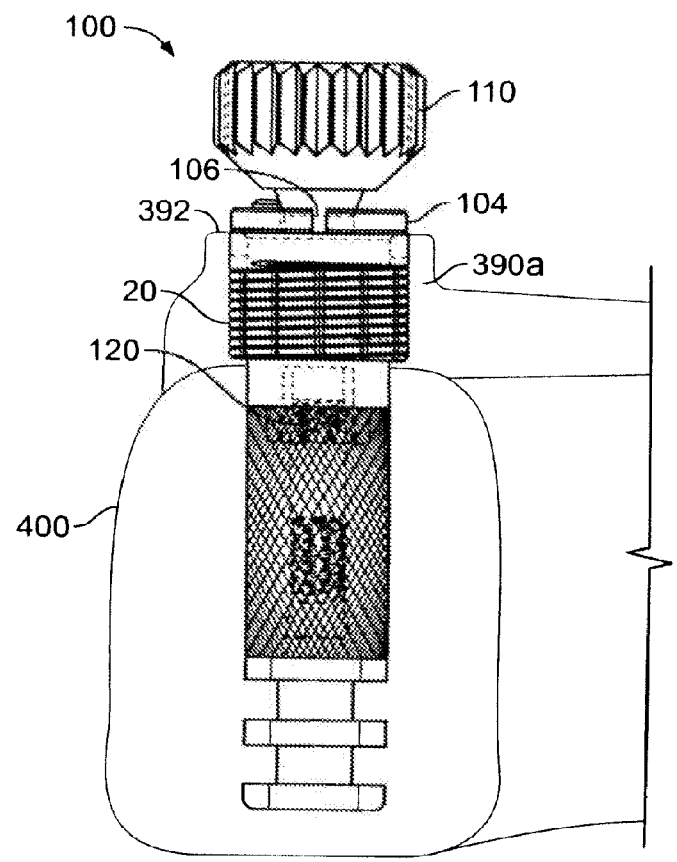
FIGS. 13A-13B illustrate the combination of the implant analogs and associated mounts of FIG. 6 after being placed in the master cast of FIG. 11.
Figure 13B:
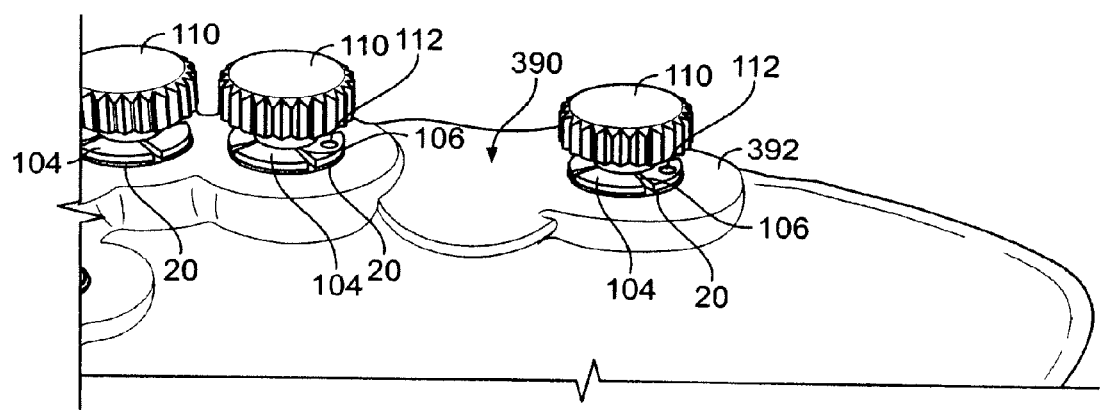

Referring back to FIGS. 1-6 as needed, FIG. 12 shows a method of forming a surgical guide from the master cast 400 according to one process. At step s450, implant-analog mounts 100 (see FIGS. 13A-13B) are attached to the master cast 400, and master tubes 20 are attached to implant analog mounts 100. The master tubes 20 are locked onto the implant analog mounts 100 due to the expansion of the top portion of the implant analog mount 100 as the implant analog mount screw is threaded into the implant analog 120. The implant analog mount screw essentially acts as a wedge within the body of the implant analog mount 100, and the top portion of the body of the implant analog mount 100 is able to expand because it is slotted. FIGS. 13A-13B illustrate the implant-analog mounts 100 and implant analogs 120 located within the master cast 400 of FIG. 11. The top flange of the expandable top section 104 rests on the master tube 20 with the orientation pin 112 fitting within one of the two notches 84 of the master tube 20. As such, the location of the non-rotation feature 122 of the implant analog 120 is known and fixed relative to the master cast 400. Once properly seated, the large rotatable head 110 is rotated a bit more (typically less than one-half revolution) to cause the expandable top section 104 to expand outwardly into the master tube 20 and lock itself into axial position.

A polymeric material 390a such as acrylic (or another suitable material) is then poured over the master cast 400 and around master tubes 20 of FIGS. 13A-13B to form a surgical guide 390 (see FIG. 14) at step s452. Preferably, the master tubes 20 are placed in the surgical guide 390 such that their uppermost surfaces are located on flat surfaces 392 (see also FIG. 14) of the surgical guide 390. Once all of the polymeric material 390a has hardened and cured, the large rotatable head 110 of the implant-analog mount 100 may be loosened, which unlocks the implant-analog mount 100 from the master tube 20 and eventually releases the implant-analog mount 100 from the implant analog 120 such that the resulting surgical guide 390 may be removed from the master cast 400 and the implant-analog mount 100 may be removed from the surgical guide 390 at step s454.

The resulting surgical guide 390 fits snugly onto the patient's gingival surface by having a negative impression that incorporates the details of the gingival surface in the patient's mouth. Because in the illustrated embodiment, there is a need for eight implants 10, the surgical guide 390 includes eight openings, each of which is defined by a master tube 20 that is integrated into the material of the surgical guide 390 with the assistance of the outer roughened surface and/or adhesive. As described above, the end result is that the eight dental implants 10 are installed in the patient's maxilla at the depths and angles defined by the surgical plan, and the eight dental implants 10 may then be attached to a bar structure that is part of the denture-type dental prosthesis that is developed for that particular patient. Alternatively, dental abutments and/or individual prostheses may be attached to the dental implants 10.

The under portion of the surgical guide 390 (not visible in FIG. 14) has a contour that follows the master cast 400 and, thus, the scanned gingival surface in the patient's mouth. In other words, the under portion of the surgical guide 390 is a negative impression of the gingival surface of the patient's mouth.

The surgical guide 390 of FIG. 14 also includes a plurality of openings 394 through which temporary fixation screws or pins may be placed. The temporary fixation screws or pins engage the bone and hold the surgical guide 390 in the proper location on the gingival surface so that the surgical plan may be executed using the surgical guide 390. As previously mentioned, the surgical guide 390 may also be a negative impression of the surface of adjacent teeth and bone tissue in some situations and rest against the adjacent teeth and bone tissue.

As previously indicated, the implant mounts 40 of FIG. 2 are available in various lengths so that a suitable combination may be identified for each case. Dimension "E" of FIG. 1B simply needs to be greater than or equal to the height of the master tube 20 plus the distance from the implant (or analog) seating surface to the highest point on the surrounding gingival margin.

Figure 15:
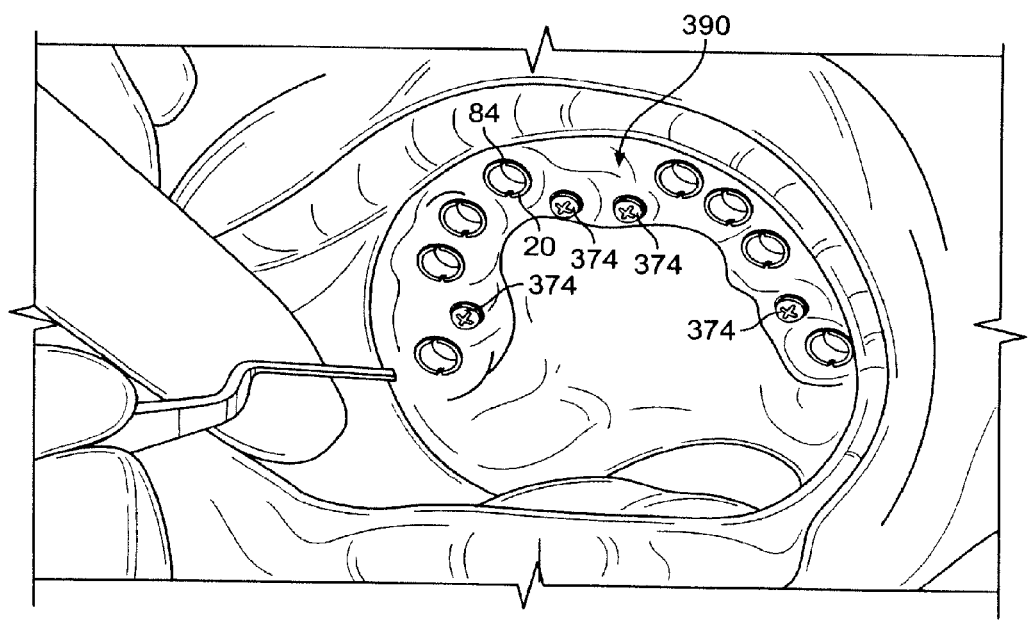
FIG. 15 illustrates the surgical guide of FIG. 14 fixed in the patient's mouth.

FIG. 15 illustrates the surgical guide 390 positioned within a patient's mouth. A clinician is generally given a set of instructions, in accordance with the surgical plan, for placing each dental implant 10 with a specific sequence of guide-tube tools and drill bits (along with other components and tools). Each implant is attached to a specifically-sized implant mount 40 in accordance to the plan. In particular, the implant 10 is screwed into the bone by use of a tool that engages the driving element 48 of the implant mount 40. Because the underlying non-rotational feature 12 of the implant 10 (FIG. 1) is aligned with the notch 47, the non-rotational feature 12 is oriented in the exact location defined by the surgical plan by aligning the notch 47 of the implant mount 40 with the notch 84 in the master tube 20.

The implants 10 may then be fitted with a temporary prosthesis crafted by the clinician using common abutments. Or, the implants 10 may receive a healing cap or healing abutment to allow for a period of osseointegration before a temporary or final prosthesis is fitted. As previously discussed, because the implant mount 40 has a known length, the exact depth of the implant 10 within the osteotomy is also known, as defined by the surgical plan for that patient.

Once all of the implants 10 are installed or after each implant is installed, the implant mounts 40 may be released from the dental implants 10 by unscrewing each of the screws 49 (FIGS. 2-3). Additionally, the surgical guide 390 may be removed from the patient's mouth by removal of the temporary fixation screws or pins from the holes 394 in the surgical guide 390.

Because each of the implants 10 are at known locations and have known orientations defined by the surgical guide 390 in accordance with the surgical plan, the patient may be immediately fitted with a prosthesis that was previously made in accordance to the surgical plan. As an example, a bar structure may be placed on the implants 10 in the patient's mouth. Eight attachment regions of the bar would fit accurately on the dental implants 10 and would be coupled to the dental implants 10 through typical dentals screws. A temporary or final denture would then be snapped on the bar structure such that the patient would have a workable set of prosthetic teeth that are defined by the surgical plan.

The embodiments and processes of the present invention are also useful for developing and installing one or more single-tooth prosthetic devices or one or more multi-tooth prosthetic devices in a patient. In other words, the surgical guide 390 may be smaller such that it only covers a limited portion of the dental arch.

In summary, using a 3-D anatomic model incorporates accurate hard tissue data and soft tissue data to create a surgical plan and then form a master cast 400 (from the surgical plan and a scan of the pre-surgical anatomic cast) having master tubes 20 that allow for the known orientation of the virtual implants 10 and the implant analogs 120. A surgical guide 390 may then be accurately developed to replicate the desired conditions in the patient's mouth in accordance with the 3-D anatomic digital model. The surgical guide 390 may then be fitted to a patient's mouth and the implants 10 may be installed in the patient's mouth in substantially the identical location, position, and orientation as the virtual implants of the surgical plan. The prosthetic device may then be fitted to the implants 10 that have been installed in the patient's mouth.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of developing a 3-D anatomic model of a patient's mouth for use in developing a dental restoration, the method comprising the acts of:
   receiving a first dataset including data associated with bone tissue and teeth, the first dataset being derived from at least one scan of the inside of the patient's mouth;
   receiving a second dataset including data associated with a gingival surface, the second dataset being derived from one or more of the at least one scan of the inside of the patient's mouth;
   merging the first dataset with the second dataset to form a combined dataset;
   removing overlapping data from the combined dataset to form a modified dataset;
   after the merging of the datasets, determining a thickness of the soft tissue from the region between the gingival surface and the jawbone; and
   displaying, on a display, the 3-D anatomic model of the patient's mouth, the 3-D anatomic model including a simulation of the bone tissue, the teeth, the gingival surface, and the gingival tissue between the bone tissue and the gingival surface with the determined thickness.

2. The method of claim 1, wherein the at least one scan is a first scan including the data associated with bone tissue and teeth and a second scan including the data associated with the gingival surface.

3. The method of claim 2, wherein the first scan is a computed tomography scan and the second scan is an intra-oral scan.

4. The method of claim 2, wherein the first scan is a computed tomography scan and the second scan is one of a scan of a dental impression of the patient's mouth or a scan of a cast model of the patient's mouth.

5. The method of claim 1, wherein the displaying the 3-D anatomic model includes filling-in a region between the gingival surface and the bone tissue to display the determined thickness of the gingival tissue.

6. The method of claim 1, further comprising displaying, on the display, an opening through the displayed gingival tissue of the 3-D anatomic model, the opening being at a location corresponding to the dental restoration.

7. The method of claim 6, further comprising displaying, on the display, a virtual custom abutment in the opening, the opening having a size and shape dictated by a size and shape of the virtual custom abutment.

8. The method of claim 7, further comprising using the 3-D anatomic model to create a surgical guide that guides the installation of a dental implant in the patient's mouth, the dental implant being a part of the dental restoration.

9. The method of claim 7, further comprising deriving a custom abutment from the virtual custom abutment, the custom abutment being a part of the dental restoration.

10. The method of claim 1, further comprising developing a custom abutment by use of the 3-D anatomic model, the custom abutment being depicted as a virtual custom abutment in the 3-D anatomic model.

11. A method of developing a 3-D anatomic model of a patient's mouth for use in developing a dental restoration, comprising the acts of:
    receiving a first dataset derived from a computed tomography scan, the first dataset being associated with bone tissue and teeth within the patient's mouth;
    receiving a second dataset derived from an intra-oral scan of the patient's mouth, the second dataset being associated with a gingival surface and the teeth within the patient's mouth;
    by use of a shape-matching algorithm that focuses on features common to the first dataset and second dataset, merging the first dataset and the second dataset, the common features including at least one existing tooth;
    by use of the first dataset and the second dataset, determining a thickness of the soft tissue in regions of the patient's mouth adjacent to a location for the dental restoration;
    after the merging, removing data that is common to the first dataset and the second dataset; and
    displaying, on a display, the 3-D anatomic model of the patient's mouth, the 3-D anatomic model including a simulation of the bone tissue, the teeth, the gingival surface, and the gingival tissue between the bone tissue and the gingival surface with the determined thickness.

12. The method of claim 10, further comprising displaying, on the display, an opening through the gingival tissue, the opening having a size and shape dictated by size and shape of the virtual custom abutment.

13. The method of claim 12, further comprising displaying, on the display, a virtual dental implant structure that corresponds to a dental implant to be placed in the patient's mouth.

14. The method of claim 13, wherein the virtual custom abutment is displayed on the display as being coupled to the virtual dental implant structure and extending through the opening in the gingival tissue.

15. The method of claim 13, further comprising using the 3-D anatomic model to create a surgical guide configured to guide the installation of the dental implant in the patient's mouth.

16. The method of claim 11, wherein the displaying the 3-D anatomic model includes filling-in a region between the gingival surface and the bone tissue to display the determined thickness of the gingival tissue.

17. The method of claim 11, further comprising displaying, on the display, an opening through the displayed gingival tissue of the 3-D anatomic model, the opening being at a location corresponding to the dental restoration.

18. The method of claim 17, further comprising displaying, on the display, a virtual custom abutment in the opening, the opening having a size and shape dictated by a size and shape of the virtual custom abutment.

19. The method of claim 18, further comprising
  using the 3-D anatomic model to create a surgical guide that guides the installation of a dental implant in the patient's mouth, the dental implant being a part of the dental restoration.

20. The method of claim 18, further comprising deriving a custom abutment from the virtual custom abutment, the custom abutment being a part of the dental restoration.

* * * * *

UNITED STATES PATENT AND TRADEMARK OFFICE
CERTIFICATE OF CORRECTION

| | | |
|---|---|---|
| PATENT NO. | : 8,651,858 B2 | Page 1 of 1 |
| APPLICATION NO. | : 12/937942 | |
| DATED | : February 18, 2014 | |
| INVENTOR(S) | : Berckmans et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 491 days.

Signed and Sealed this
Second Day of June, 2015

Michelle K. Lee
*Director of the United States Patent and Trademark Office*